United States Patent
Blatter et al.

(10) Patent No.: US 7,131,959 B2
(45) Date of Patent: Nov. 7, 2006

(54) APPARATUS AND METHODS FOR OCCLUDING AN ACCESS TUBE ANASTOMOSED TO SIDEWALL OF AN ANATOMICAL VESSEL

(75) Inventors: Duane D. Blatter, Salt Lake City, UT (US); Troy J. Orr, Draper, UT (US); Michael C. Barrus, Centerville, UT (US)

(73) Assignee: Integrated Vascular Interventional Technologies, L.C., ("IVIT LC"), Salt Lake City, UT (US)

( * ) Notice: Subject to any disclaimer, the term of this patent is extended or adjusted under 35 U.S.C. 154(b) by 429 days.

(21) Appl. No.: 10/351,172

(22) Filed: Jan. 23, 2003

(65) Prior Publication Data
US 2004/0147866 A1 Jul. 29, 2004

(51) Int. Cl.
*A61M 37/00* (2006.01)
*C02F 1/44* (2006.01)
*A61B 17/08* (2006.01)

(52) U.S. Cl. .................... 604/6.16; 604/4.01; 210/645; 606/153

(58) Field of Classification Search .............. 604/4.01, 604/5.01, 6.05, 6.06, 6.1, 6.16, 7–10, 27, 604/28, 43, 175, 506–509, 5.04, 21, 32–34, 604/96.01, 101.04, 103.07, 288.1, 891.1, 604/103.01, 30, 93.01, 264; 606/153, 157, 606/139; 623/1.13, 1.36, 1.25, 1.24, 1.42; 210/600, 645, 646
See application file for complete search history.

(56) References Cited

U.S. PATENT DOCUMENTS

| | | | |
|---|---|---|---|
| 3,392,722 A | 7/1968 | Jorgensen | |
| 3,395,710 A | 8/1968 | Stratton et al. | |
| 3,713,441 A * | 1/1973 | Thomas | 604/8 |
| 3,826,257 A | 7/1974 | Buselmeier | |
| 3,853,126 A * | 12/1974 | Schulte | 604/8 |
| 3,991,756 A | 11/1976 | Synder | |
| 4,122,858 A | 10/1978 | Schiff | |
| 4,301,797 A | 11/1981 | Pollack | |
| 4,318,401 A * | 3/1982 | Zimmerman | 604/28 |
| 4,366,819 A | 1/1983 | Kaster | |
| 4,370,983 A | 2/1983 | Lichtenstein | |
| 4,421,507 A | 12/1983 | Bokros | |
| 4,623,348 A | 11/1986 | Feit | |
| 4,655,771 A | 4/1987 | Wallsten | |

(Continued)

FOREIGN PATENT DOCUMENTS

WO    WO 98/19629    5/1998

(Continued)

OTHER PUBLICATIONS

Lycos, Your Personal Internet Guide, APHERESIS, located at http://infoplease.lycos.com/ipd/A0321273.html, 1 pg, printed Jun. 12, 2003.

(Continued)

*Primary Examiner*—Tatyana Zalukaeva
*Assistant Examiner*—Leslie R. Deak
(74) *Attorney, Agent, or Firm*—Stoel Rives LLP

(57) ABSTRACT

The invention provides vascular access methods, systems and devices facilitating long-term, repeated, percutaneous access to a patient's blood stream. This is provided by an access tube apparatus adapted for anastomosis to the sidewall of a target anatomical vessel. The access tube has a replaceable occluder that fits within the conduit of the access tube in between blood treatments or when vascular access is otherwise not needed. When such access is desired, the percutaneously accessible occluder is simply removed from the access tube.

47 Claims, 19 Drawing Sheets

U.S. PATENT DOCUMENTS

| | | | |
|---|---|---|---|
| 4,819,637 A | 4/1989 | Dormandy, Jr. et al. | |
| 4,822,341 A | 4/1989 | Colone | |
| 4,846,186 A | 7/1989 | Box et al. | |
| 5,092,841 A | 3/1992 | Spears | |
| 5,102,402 A | 4/1992 | Dror et al. | |
| 5,290,306 A | 3/1994 | Trotta et al. | |
| 5,304,220 A | 4/1994 | Maginot | |
| 5,411,475 A | 5/1995 | Atala et al. | |
| 5,417,657 A | 5/1995 | Hauer | |
| 5,443,497 A | 8/1995 | Venbrux | |
| 5,456,712 A | 10/1995 | Maginot | |
| 5,458,568 A | 10/1995 | Racchini et al. | |
| 5,478,320 A | 12/1995 | Trotta | |
| 5,613,979 A | 3/1997 | Trotta et al. | |
| 5,616,114 A | 4/1997 | Thornton et al. | |
| 5,617,878 A | 4/1997 | Taheri | |
| 5,620,649 A | 4/1997 | Trotta | |
| 5,634,936 A | 6/1997 | Linden et al. | |
| 5,662,580 A | 9/1997 | Bradshaw et al. | |
| 5,662,700 A | 9/1997 | Lazarus | |
| 5,693,088 A | 12/1997 | Lazarus | |
| 5,695,504 A | 12/1997 | Gifford, III et al. | |
| 5,702,412 A | 12/1997 | Popov et al. | |
| 5,755,775 A | 5/1998 | Trerotola et al. | |
| 5,766,158 A | 6/1998 | Opolski | |
| 5,779,731 A | 7/1998 | Leavitt | |
| 5,792,095 A | 8/1998 | Kissinger et al. | |
| 5,795,325 A | 8/1998 | Valley et al. | |
| 5,797,879 A | 8/1998 | DeCampli | |
| 5,797,934 A | 8/1998 | Rygaard | |
| 5,817,113 A | 10/1998 | Gifford, III et al. | |
| 5,830,222 A | 11/1998 | Makower | |
| 5,830,228 A | 11/1998 | Knapp et al. | |
| 5,843,027 A | 12/1998 | Stone et al. | |
| 5,868,770 A | 2/1999 | Rygaard | |
| 5,893,369 A | 4/1999 | LeMole | |
| 5,925,060 A | 7/1999 | Forber | |
| 5,954,706 A | 9/1999 | Sahatjian | |
| 5,961,536 A | 10/1999 | Mickley et al. | |
| 5,976,178 A | 11/1999 | Goldsteen et al. | |
| 6,007,576 A | 12/1999 | McClellan | |
| 6,030,392 A | 2/2000 | Dakov | |
| 6,042,569 A | 3/2000 | Finch, Jr. et al. | |
| 6,063,114 A * | 5/2000 | Nash et al. | 623/1.36 |
| 6,068,637 A | 5/2000 | Popov et al. | |
| 6,086,553 A | 7/2000 | Akbik | |
| 6,102,884 A * | 8/2000 | Squitieri | 604/8 |
| 6,113,612 A | 9/2000 | Swanson et al. | |
| 6,171,319 B1 | 1/2001 | Nobles et al. | |
| 6,200,257 B1 | 3/2001 | Winkler | |
| 6,210,365 B1 | 4/2001 | Afzal | |
| 6,214,022 B1 * | 4/2001 | Taylor et al. | 606/153 |
| 6,248,117 B1 | 6/2001 | Blatter | |
| 6,254,563 B1 | 7/2001 | Macoviak et al. | |
| 6,261,257 B1 | 7/2001 | Uflacker et al. | |
| 6,264,633 B1 | 7/2001 | Knorig | |
| 6,280,460 B1 | 8/2001 | Bolduc et al. | |
| 6,293,965 B1 | 9/2001 | Berg et al. | |
| 6,319,226 B1 | 11/2001 | Sherry | |
| 6,401,721 B1 | 6/2002 | Maginot | |
| 6,595,941 B1 | 7/2003 | Blatter | |
| 6,656,151 B1 | 12/2003 | Blatter | |
| 6,663,590 B1 | 12/2003 | Blatter | |
| 6,746,459 B1 | 6/2004 | Kato | |
| 2002/0049459 A1 | 4/2002 | Kato | |

FOREIGN PATENT DOCUMENTS

| | | |
|---|---|---|
| WO | WO 98/19634 | 5/1998 |

OTHER PUBLICATIONS

Clark Biocompatible Hemoperfusion System and Block Cutter, *Some Other Products from Clark Research, Clark® Biocompatible Hemoperfusion*, located at http://www.clarkrd.com/crd_other2.htm, 10 pgs., printed Jun. 24, 2003.

HGSA, *Medicare Medical Policy Bulletin, Policy S-107: Hemoperfusion, Bulletin, Freedom of Information*, located at http://www.hgsa.com/professionals/policy/s107.html, 1 pg., printed Jun. 24, 2003.

Facts about Plasmapheresis, *Plasmapheresis and Autoimmune Disease*, MDA Publications, located at http://www.mdausa.org/publications/fa-plasmaph.html, 4 pgs., printed Apr. 16, 2003.

Publications, *Hemodialysis*, located at http://www.rein.ca/hem-e.htm, 4 pgs., printed Apr. 16, 2003.

Tennesse Kidney Clinics and Affiliates, *What is Hemodialysis?* located at http://www.dialysisclinics.com/hemo.htlm, 2 pgs., printed Jun. 24, 2003.

*Good Nutrition & Hemodialysis*, located at http://www.nyu.edu/classes/compnutrfood/Cecilia%20Fong/index.html 1 pg., printed Jun. 24, 2003.

Mulzer, S.R. and Brash, J.L., *Identification of Plasma Proteins Adsorbed to Hemodialyzers During Clinical Use*, Journal of Biomedical Materials Research, vol. 23, 1483-1504 (1989).

Ljungberg, B., et al., *Effective Anticoagulation by a low Molecular Weight Heparin (Fragmin®) in Hemodialysis with a Highly Permeable Polysulfone Membrane*, Clinical Nephrology, vol. 38, No. 2-1992 (97-100).

Jen Ming Yang, et al., *Preparation of Heparin Containing SBS-g-VP Copolymer Membrane for Biomaterial Usage*, Journal of Membrane Science 138 (1998) 19-27.

Office Action dated Sep. 29, 2005 in U.S. Appl. No. 10/624,711, 7 pgs.

Interview Summary from Oct. 18, 2005 in U.S. Appl. No. 10/624,711, 1 pg.

Office Action Response dated Dec. 15, 2005 in U.S. Appl. No. 10/624,711, 16 pgs.

Office Action dated Sep. 20, 2005 in U.S. Appl. No. 10/624,315, 7 pgs.

Interview Summary dated Oct. 18, 2005 in U.S. Appl. No. 10/624,315, 1 pg.

Office Action Response dated Dec. 16, 2005 in U.S. Appl. No. 10/624,315, 19 pgs.

Office Action dated Sep. 20, 2005 in U.S. Appl. No. 10/624,315, 7 pgs.

Interview Summary from Oct. 18, 2005 in U.S. Appl. No. 10/624,315, 1pg.

Office Action Response dated Dec. 16, 2005 in U.S. Appl. No. 10/624,315, 19 pgs.

Office Action dated Sep. 29, 2005 in U.S. Appl. No. 10/624,711, 7 pgs.

Interview Summary from Oct. 18, 2005 in U.S. Appl. No. 10/624,711, 1 pg.

Office Action Response dated Dec. 15, 2005 in U.S. Appl. No. 10/624,711, 16 pgs.

Office Action dated Jan. 12, 2006 in U.S. Appl. No. 10/351,172, 2 pgs.

Office Action Response dated Feb. 10, 2006 in U.S. Appl. No. 10/351,172, 12 pgs.

Office Action dated Aug. 18, 2005 in U.S. Appl. No. 10/351,172, 5 pgs.

Interview Summary from Oct. 18, 2005 in U.S. Appl. No. 10/351,172, 1 pg.

Office Action Response dated Dec. 16, 2005 in U.S. Appl. No. 10/351,172, 21 pgs.

Office Action dated Jan. 29, 2002 in U.S. Appl. No. 09/481,283 (Patent No. 6,595,941), 7 pgs.

Interview Summary from Jun. 13, 2002 in U.S. Appl. No. 09/481,283 (Patent No. 6,595,941), 1 pg.
Office Action Response dated Jul. 1, 2002 in U.S. Appl. No. 09/481,283 (Patent No. 6,595,941), 13 pgs.
Office Action dated Sep. 25, 2002 in U.S. Appl. No. 09/760,322 (Patent No. 6,663,590), 9 pgs.
Interview Summary from Nov. 21, 2002 in U.S. Appl. No. 09/760,322 (Patent No. 6,663,590), 1 pg.
Office Action Response dated Mar. 25, 2003 in U.S. Appl. No. 09/760,322 (Patent No. 6,663,590), 31 pgs.
Office Action dated Jun. 18, 2003 in U.S. Appl. No. 09/760,322 (Patent No. 6663590), 4 pgs.
Office Action Response dated Jun. 26, 2003 in U.S. Appl. No. 09/760,322 (Patent No. 6,663,590), 2 pgs.
Office Action (Election/Restrictions) dated Apr. 10, 2001 in U.S. Appl. No. 09/480,964 (Patent No. 6,656,151), 4 pgs.
Response to Restriction Requirement dated Jul. 10, 2001 in U.S. Appl. No. 09/480,964, (Patent No. 6,656,151) 2 pgs.
Office Action dated Sep. 13, 2001 in U.S. Appl. No. 09/480,964 (Patent No. 6,656,151), 6 pgs.
Office Action Response dated Mar. 13, 2002 in U.S. Appl. No. 09/480,964 (Patent No. 6,656,151), 8 pgs.
Interview Summary from Mar. 13, 2002 in U.S. Appl. No. 09/480,964 (Patent No. 6,656,151), 1 pg.
Final Office Action dated Apr. 9, 2002 in U.S. Appl. No. 09/480,964 (Patent No. 6,656,151), 7 pgs.
Final Office Action dated Oct. 1, 2002 in U.S. Appl. No. 09/480,964 (Patent No. 6,656,151), 7 pgs.
Interview Summary from Nov. 21, 2002 in U.S. Appl. No. 09/480,964 (Patent No. 6,656,151), 1 pg.
Office Action Response dated Apr. 1, 2003 in U.S. Appl. No. 09/480,964 (Patent No. 6,656,151), 36 pgs.
Interview Summary from May 6, 2003 in U.S. Appl. No. 09/480,964 (Patent No. 6,656,151), 1 pg.

* cited by examiner

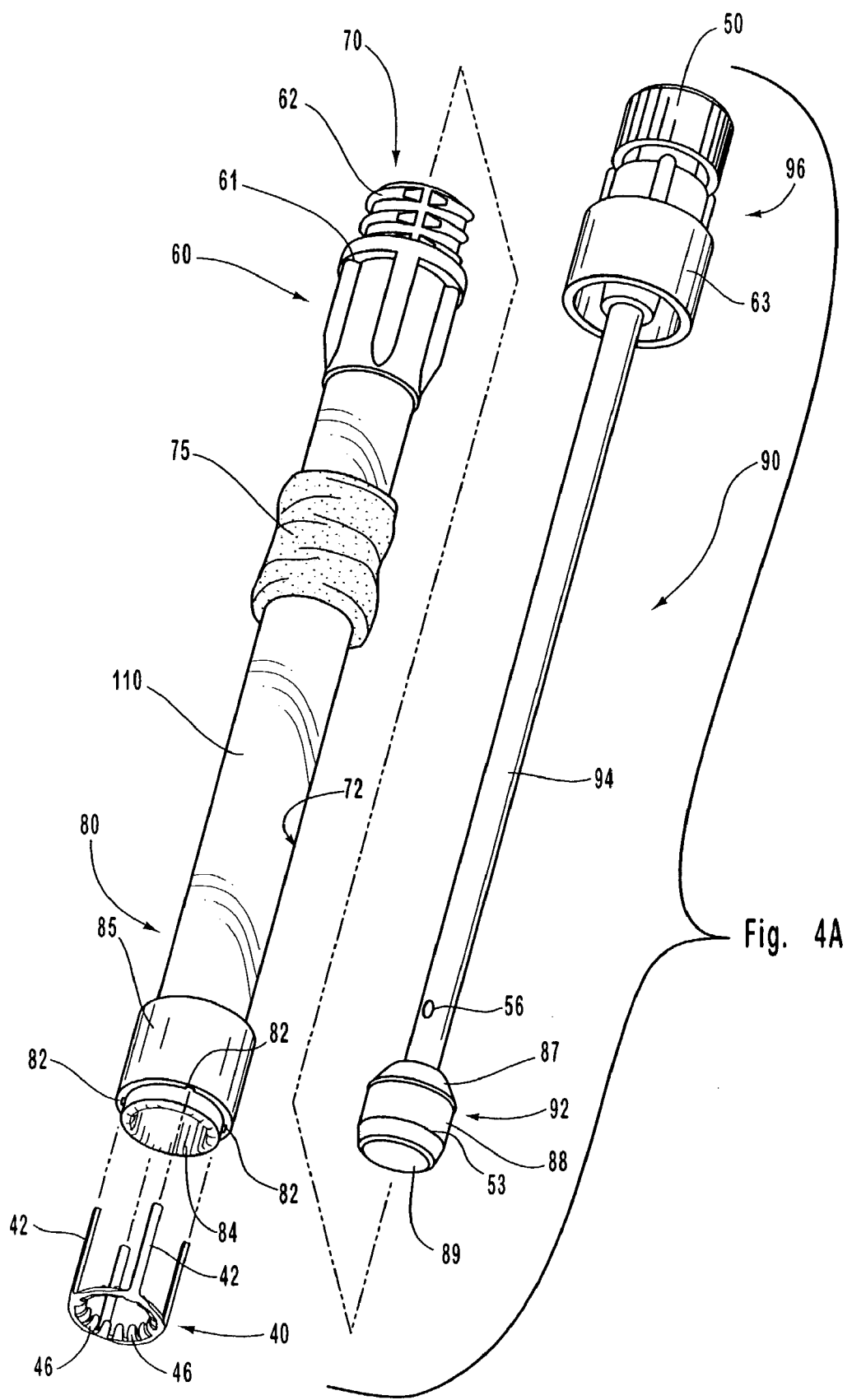

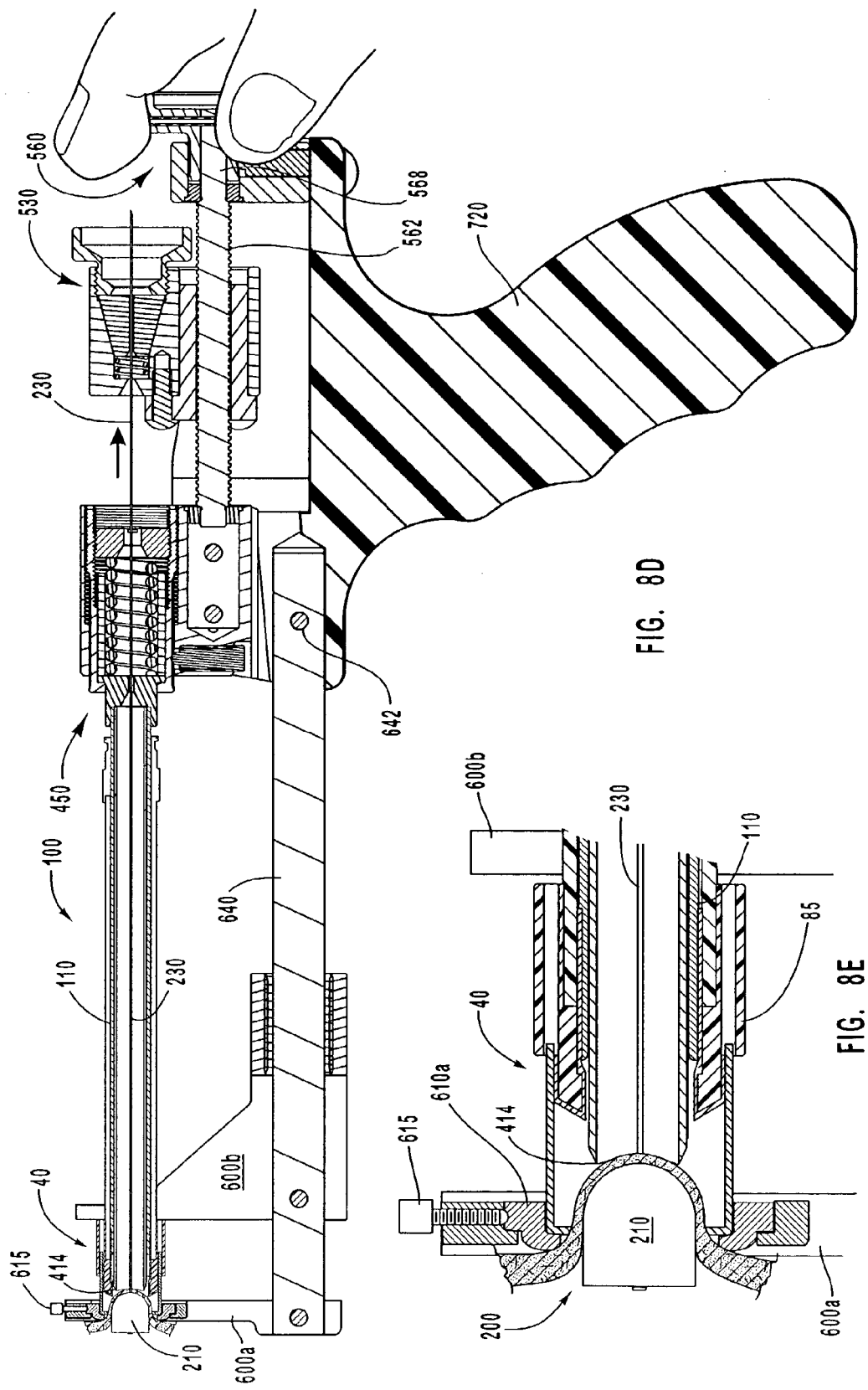

APPARATUS AND METHODS FOR OCCLUDING AN ACCESS TUBE ANASTOMOSED TO SIDEWALL OF AN ANATOMICAL VESSEL

TECHNICAL FIELD

The present invention relates to vascular access methods and apparatus. More particularly, it relates to such methods and apparatus that allow for repeated percutaneous access to an anatomical vessel such that repeated punctures of the vessel and/or the patient's skin are not necessary.

BACKGROUND OF THE INVENTION

Examples of procedures that require repeated access to anatomical vessels include dialysis and the delivery of medicines for an extended period of time. The multiple punctures that such repeated access necessitates eventually render the accessed vessels unsuitable for further effective injections. Accordingly, there is a need for apparatus, methods, and systems for facilitating long-term, repeated vascular access.

Dialysis procedures, for example, typically employ catheters, which are inserted into a patient's bloodstream to withdraw blood for treatment and then return treated blood back into the bloodstream. However, there are a number of drawbacks to such catheter systems. For example, because the catheters of such systems are inserted directly into the lumen of a patient's blood vessel, they obstruct blood flow in the vessels. Therefore, the diameter of catheters available for dialysis is quite limited. A dialysis catheter must be sufficiently small to allow for a relatively smooth path for blood flow around the catheter. Because high flow rates through catheters are desirable to maximize the efficiency of dialysis procedures, this limitation is disadvantageous.

Dialysis procedures and systems utilizing catheters have a number of other disadvantages. For example, because the catheters of such systems are inserted directly into a patient's bloodstream, they are susceptible to developing thrombi, infection, and/or other complications. In addition, prior to each treatment with a conventional catheter dialysis system, the patient's skin and blood vessel must be punctured in one or more locations. These repeated punctures can damage a patient's blood vessels to the extent that they can no longer withstand further punctures. Also, repeated punctures of a patient's skin can be painful and can likewise damage the skin. Moreover, because the repeated use of larger needles and catheters causes greater damage to a patient's blood vessels and skin, this further limits the effectiveness of conventional dialysis procedures.

One solution to the need for repeated access which does not employ intraluminal catheters is disclosed in U.S. Pat. No. 3,826,257 issued to Buselmeier. Buselmeier discloses a percutaneous vascular access device utilizing a U-shaped shunt tube, the ends of which are anastomosed in an end-to-end manner to the severed ends of an artery and adjacent vein. The other ends of the artery and vein are tied off and allowed to become non-functional.

There are numerous drawbacks and disadvantages to the Buselmeier device, some of which will now be discussed. First, in Buselmeier, blood flow in the shunt tube is constantly exposed to foreign or non-native surfaces which are not easily replaceable—i.e., not without further recurring surgical procedures. Because there is such a large non-native surface area exposed to blood flow in the vessel, and because those surfaces that are exposed are not easily replaceable, the Buselmeier device is prone to complications such as thrombosis, blood stagnation, and infection. The only way to prevent or control such complications would be to replace the device, which requires an invasive surgical procedure. A replacement surgery would be needed on a more frequent periodic basis than would be practical. Moreover, the surgeries themselves tend to cause trauma to the vessels being accessed, which may ultimately leave them unsuitable for further access. For at least these reasons, the Buselmeier configuration is not suitable for effective long-term vascular access.

In addition, the Buselmeier device has blood from an artery re-routed directly into a vein. The characteristics of the fluid flow in an artery are significantly different from the characteristics of the fluid flow in a vein. These fluid flow dissimilarities may lead to additional adverse effects that detrimentally affect the long term accessibility of the blood vessels that must be accessed for the external blood treatment to be effectively performed. For example, in an arteriovenous (AV) graft constructed as a vascular access for dialysis, the blood flow and blood pressure characteristic of the arterial circulation are so different from the blood flow and blood pressure in the vein into which the blood of the AV graft flows that the vein usually develops hyperplasia and stenoses. Because of these fluid flow dissimilarities, it is preferable to avoid the detrimental impact on the vessels and their long-term accessibility caused by the Buselmeier configuration, even apart from the persistent surgical procedures needed to avoid the blood-flow complications discussed above.

It is therefore desirable to provide devices, systems, and methods that permit repeated access to a blood vessel or other anatomical vessel for external treatment, such as hemodialysis, in such a way that the vessel being accessed is available for successive dialysis operations. Moreover, it is desirable, particularly from a patient's perspective, to provide such devices, systems, and methods wherein access to a blood vessel is obtained without the need for puncturing the patient's skin and blood vessels each time access is needed.

It is also desirable to provide devices, systems and methods that permit repeated access to a blood vessel for the purpose of delivering medicines into the patient's blood stream in such a way that the receiving blood vessel is not so severely damaged that it cannot be used after a few administrations of medicine.

Furthermore, it would be desirable to provide a device that is suitable for repeated vascular access for the purpose of long term medicine delivery into the patient's blood flow and also for the purpose of effectively practicing hemodialysis for a long period of time. It would also be advantageous to provide such a device that can be connected to any of several veins and/or arteries or a combination thereof as desired. In addition, it would be desirable to provide such a device or system wherein the hemodialysis procedure could be completed without obstructing the flow of blood in the patient's bloodstream and thereby limiting the diameter of available tubes for blood transport.

The practical advantages of such devices and systems would be considerably enhanced if the device or system is reliably attachable to a blood vessel. These goals should be accomplished while minimizing, or avoiding to the maximum extent possible, undesirable adverse effects such as vessel thrombosis, blood stagnation, the formation of undesirable blood disturbances, and infection. Such complications are minimized by providing a configuration designed to minimize the exposure of the blood stream to non-native materials between accesses and can be further minimized by providing a configuration wherein the only non-native surface area exposed to blood flow is replaceable.

The prior art has yet to provide an apparatus or system having the desirable characteristics discussed above. Accordingly, there is a need for methods and apparatus that provide for repeated vascular access while minimizing the problems which are associated with those of the prior art.

SUMMARY OF THE INVENTION

The present invention provides methods and apparatus for facilitating long-term, repeated vascular access while minimizing the problems typically associated with such devices. By minimizing the surface area of non-native or externally introduced material exposed to blood flow in the vessels, and by making those surfaces that are exposed easily replaceable, many complications can be controlled or eliminated.

These objects are achieved by providing an access tube apparatus that is adapted for anastomosis to the sidewall of a target blood vessel. After a hole is formed in the sidewall of the target vessel, the access tube can be anastomosed to the vessel using any desired method, including suturing, stapling, clamping, welding, adhesives, etc. In one embodiment, the access tube has an attached or integrally formed anastomosis ring with guide posts fitting within slots in an attached or integrally formed portion of the access tube to facilitate the anastomosis procedure. Once anastomosed to the target vessel sidewall, the access tube apparatus extends through the patient's skin with an access end that is externally accessible.

Fitting within the conduit of the access tube is an occluder. Preferably, the occlusion end of the occluder extends all the way to the target vessel wall without extending significantly into the vessel lumen. In other words, the occlusion end preferably abuts the target vessel wall and is approximately flush with the vessel wall such that the blood has a relatively smooth flow path around the area in which the access tube is attached to the vessel. This helps to minimize complications resulting from blood-flow disturbances.

The occluder need not be any particular size and shape. To illustrate, it may be a stemmed occluder wherein the portion between the access end and the anastomosis end has a smaller diameter than that of the occlusion end, such that a chamber is created inside the access tube conduit. In such an embodiment, while the occluder is in its occluding position in the access tube the chamber is simultaneously isolated from the outside environment and from the target vessel lumen. As an alternative, the occluder may be uniformly-shaped, such that there is no such chamber and the occluder has approximately the same diameter throughout its length. Various other embodiments are also possible, including tapered occluders, etc.

Optionally, coatings may be applied to the occluder and/or to surfaces inside the access tube conduit. For instance, coatings that include pharmacological agents such as antibacterial, antithrombotic, or antiproliferative agents may be applied to the surface of the occlusion end of the occluder. Optionally, the coatings may be configured to elute off the surface to control physiological responses. Such coatings may also be applied to surfaces inside the access tube conduit. In addition, any of the surfaces inside the access tube conduit may be coated with a lubricant to facilitate removing and inserting the occluder.

Another aspect of one embodiment of the present invention involves utilizing a flushing conduit, which may be within the stem of a stemmed occluder. This conduit opens at the access end of the access tube to a flushing port. The flushing port has a cap for sealing off the flushing conduit when not in use. At the opposite end, the conduit opens at one or more pores on the stem that terminate at the chamber in the access tube conduit. The flushing conduit can be used to introduce fluids, such as antibacterial fluids, to flush and/or sanitize the access tube conduit. The fluid can be left in the access tube conduit in between vessel accesses, or it can be flushed through the conduit and then withdrawn.

One method of the present invention utilizes two of the access tube devices discussed, one being used for extracting blood from the target vessel and the other used for inserting treated blood back into the blood stream. The second access tube used to insert the treated blood can be anastomosed to the same target vessel at a downstream location or, alternatively, it can be anastomosed to a different blood vessel. Of course, whereas the devices are typically used in connection with blood vessels, they may also be effectively employed in connection with other anatomical vessels, such as ureters/urethra, or any other anatomical vessel.

While two access tubes are typically used, it is also possible to use a single access tube. For example, only one access tube would be necessary for withdrawing particularized amounts of blood for testing, etc., or for inserting medications or other pharmacological agents into a patient's blood stream. A single access tube could also be used to both withdraw and insert blood for treatment, either simultaneously or intermittently.

Additional aspects and advantages of this invention will be apparent from the following detailed description of preferred embodiments, which proceeds with reference to the accompanying drawings.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 4A is an exploded perspective view of the access tube device with the occluder withdrawn from the access tube and the target vessel anastomosis ring withdrawn from the slots in the access tube anastomosis ring.

FIG. 8D is a cross-sectional view of the external anastomosis operator.

FIG. 8E is a partial cross-sectional view of the external anastomosis operator engaging the anvil apparatus inside the target blood vessel during an anastomosis procedure.

DETAILED DESCRIPTION OF PREFERRED EMBODIMENTS

Several different embodiments of the occludable access tube apparatus are disclosed herein. One embodiment of the apparatus of the present invention is shown in FIGS. 1–4H at 100. Other embodiments are identified as 100' and 100" respectively in FIGS. 5 and 6.

The primary components of the device include the following. First, an access tube is provided, identified generally at 110, which is adapted for anastomosis to an anatomical vessel at an anastomosis end. The anastomosis procedure is typically facilitated by the use of an anastomosis component, identified as a target vessel anastomosis ring 40 in several of the accompanying figures. The target vessel anastomosis ring may be adapted to cooperate with an access tube anastomosis ring, identified generally at 85, in accomplishing the anastomosis procedure.

Figure 5:
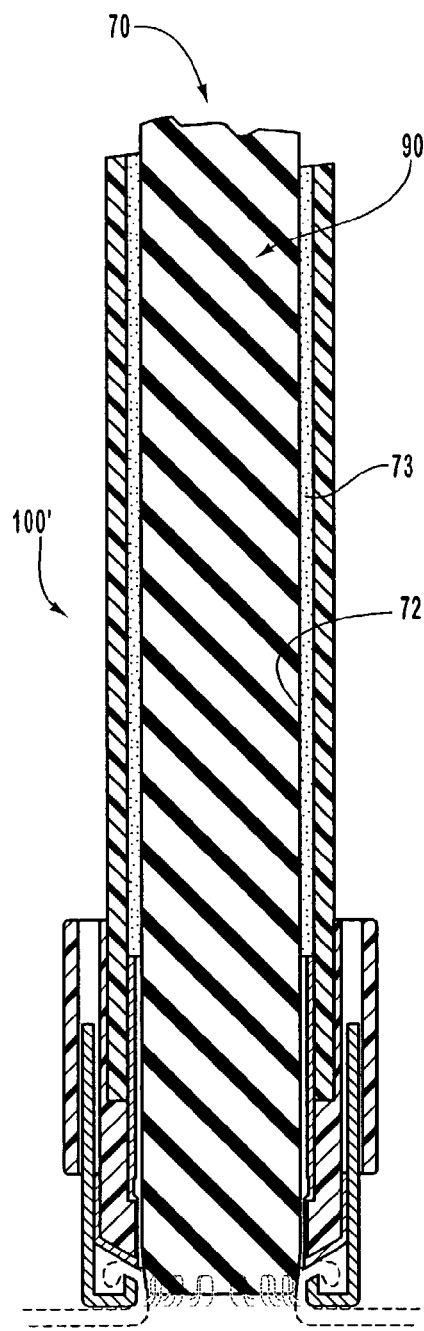
FIG. 5 is a cross-sectional view of an embodiment of the device employing a uniformly-shaped occluder with a coating.

An access end of access tube 110 opposite from an anastomosis end extends through the skin and is externally accessible. Fitting within the access tube at the access end is an occluder, identified generally at 90. The occluder is adapted to allow for selective occlusion of the conduit 70 of access tube 110 and thereby allow for selective access to the body fluid in the anatomical vessel. Anything serving these purposes is considered to be an occluder, as within the scope of the term as used herein. Another example of an occluder is shown in FIG. 5 and FIG. FIG. 6 at 90'. Occluders 90 and 90' are examples of occluding means for blocking fluid communication between the vessel and the access tube.

Figure 1:
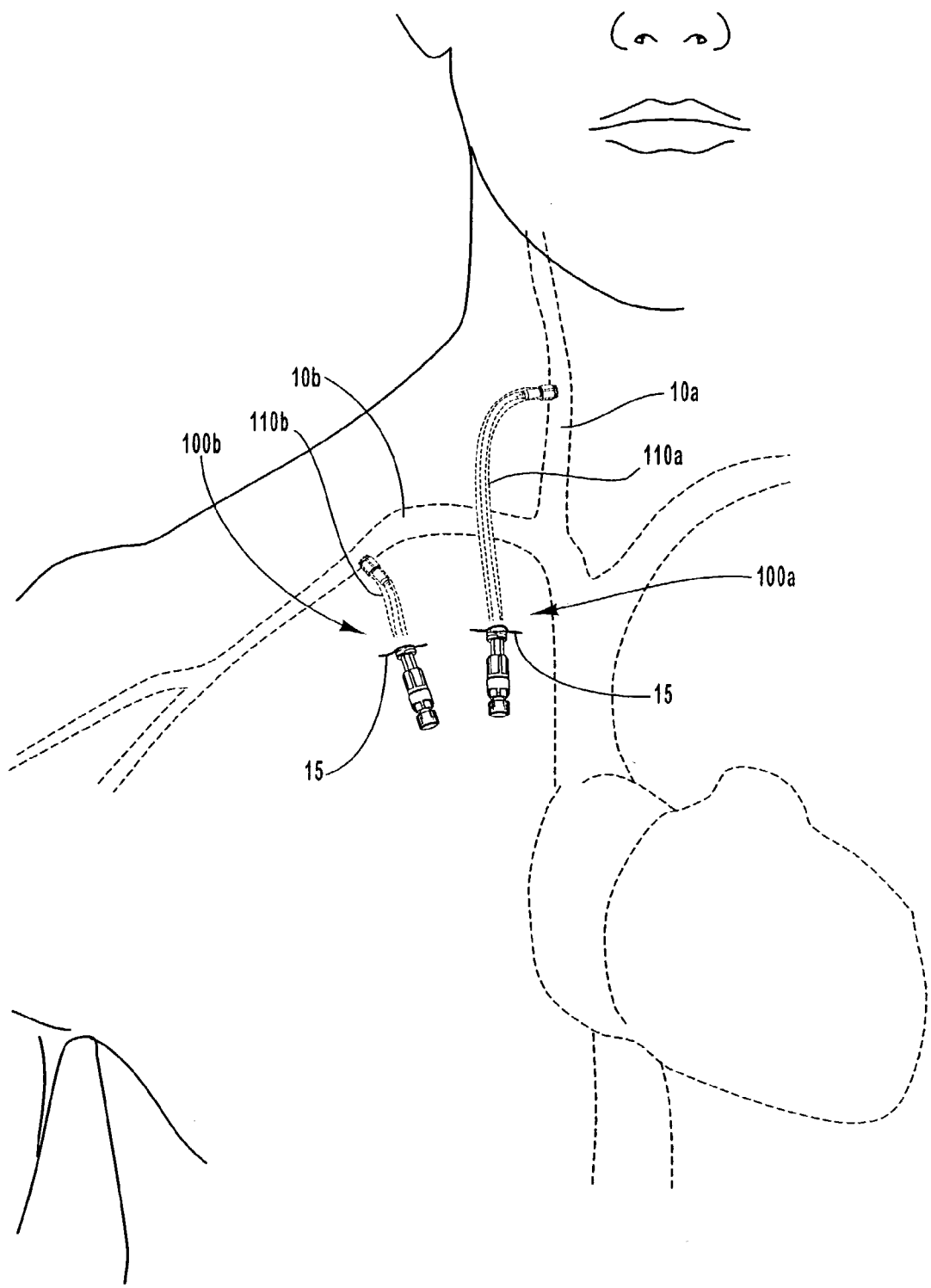
FIG. 1 is a perspective view of two access tube devices attached to a patient's blood vessels and protruding from the skin.

FIG. 1 shows two separate access tubes anastomosed to the sidewalls of two separate target blood vessels, identified at 10a and 10b in the figure. The anastomosis of the access tubes to the vessels can be done by any suitable methodology, including suturing, stapling, welding, clamping, use of adhesives, anastomosis rings and/or plates, or any other anastomosis technology currently known in the art or hereafter invented. However, in the embodiment depicted in FIG. 1, an anastomosis ring is used, which is attachable to the access tube device, in combination with another similar ring attached to, or integrally formed with, the access tube. The method for deploying this embodiment involves the use of an external anastomosis operator. Both the anastomosis ring and the external operator are discussed in greater detail later in relation to the access tubes.

Regardless of the methodology used to attach the access tube to the target vessel, however, it is preferable that the access tube not extend significantly into the target vessel lumen so as to disrupt the flow of blood or other body fluids in the vessel lumen. Accordingly, as the term is used in this context, an access tube can extend into a target vessel without extending "significantly" therein if the flow of body fluid in the access-tube region is not disrupted to the degree that it would cause complications.

While FIG. 1 shows the access tubes attached to blood vessels, the present invention can be used in connection with any anatomical vessel. To illustrate, the devices, methods, and systems disclosed herein may be used in connection with ureters, urethras, intestines, or any other vessel in the body. Thus, the present invention can provide access to body fluids other than blood. In fact, any body fluid within any anatomical vessel can be accessed by the herein disclosed apparatus, methods, and systems.

The first access tube apparatus, or extraction access tube apparatus 100a, extends from first target blood vessel 10a percutaneously—or through an incision 15 in the patient's skin—such that the access end of the first access tube is extracorporeally accessible at a first access location. Likewise, the second access tube apparatus, or insertion access tube apparatus 100b, extends from second target blood vessel 10b percutaneously such that the access end of the second access tube is also extracorporeally accessible at a second access location.

When access to the blood is not needed, and as best seen in subsequent figures, an occluder 90 having an occlusion end 92 blocks fluid communication between each of the blood vessels and the access tube conduits. In this way, when access to the blood is desired for treatment or any other reason, one need only remove the occluders from the access tube conduits to gain access.

The extracorporeally accessible ends of the access tubes may be sutured or otherwise affixed to the patient's skin. As illustrated by FIG. 1, embodiments of the present invention may be configured to be sufficiently flexible so as to allow for convenient safe-keeping of the device between uses. In such embodiments, affixing the device to the patient's skin serves to mitigate interference with the patient's everyday activities caused by the device. For instance, this feature would minimize disturbances caused by the patient's clothing with the device. In addition, it would serve a safety function, helping to prevent the device from being pulled off of the target vessel.

As should be apparent, the present invention allows for enormous flexibility in the placement positions of the access tubes. While the embodiment shown in FIG. 1 has the extraction access tube apparatus 100a anastomosed to the jugular vein in the patient's neck and the insertion access tube apparatus 100b anastomosed to the subclavian vein, countless variations are possible. To illustrate, each of the access tubes could be anastomosed to any of the various other veins and/or arteries of the body, such as those in the arms, legs, shoulders, neck, or elsewhere.

Figure 3:
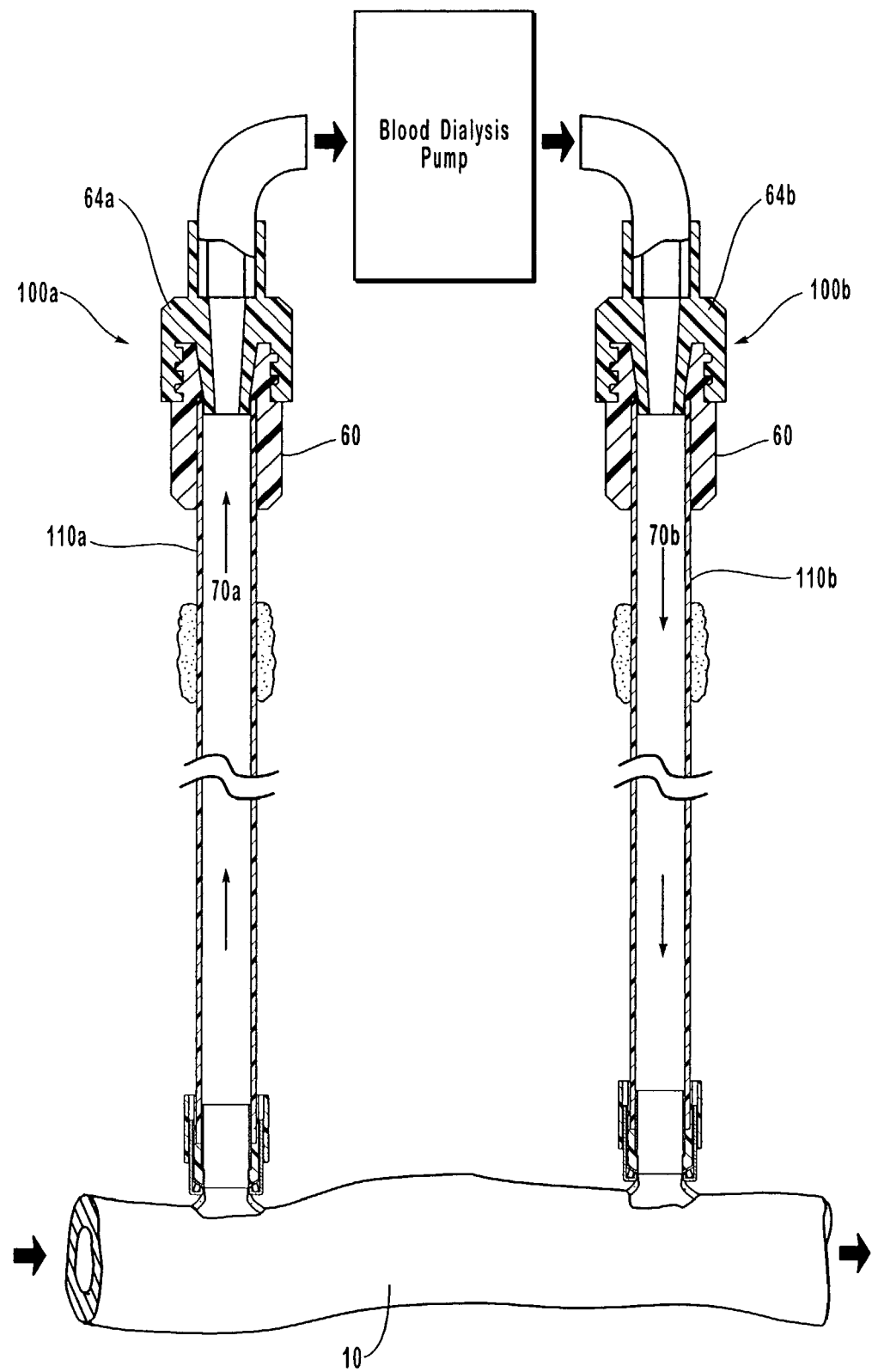
FIG. 3 is a partial cross-sectional view of the access tube devices attached to the same target vessel at two separate locations, again with their occluders withdrawn for blood treatment.

Moreover, the access tubes of the invention need not even be attached to separate vessels. FIG. 3 shows another embodiment of the occludable access tube apparatus wherein the extraction access tube apparatus and the insertion access tube apparatus are anastomosed to the same vessel 10 at separate locations, one downstream from the other. It should now be apparent that the precise location and type of vessel to which the device may be anastomosed may vary considerably.

Figure 2A:
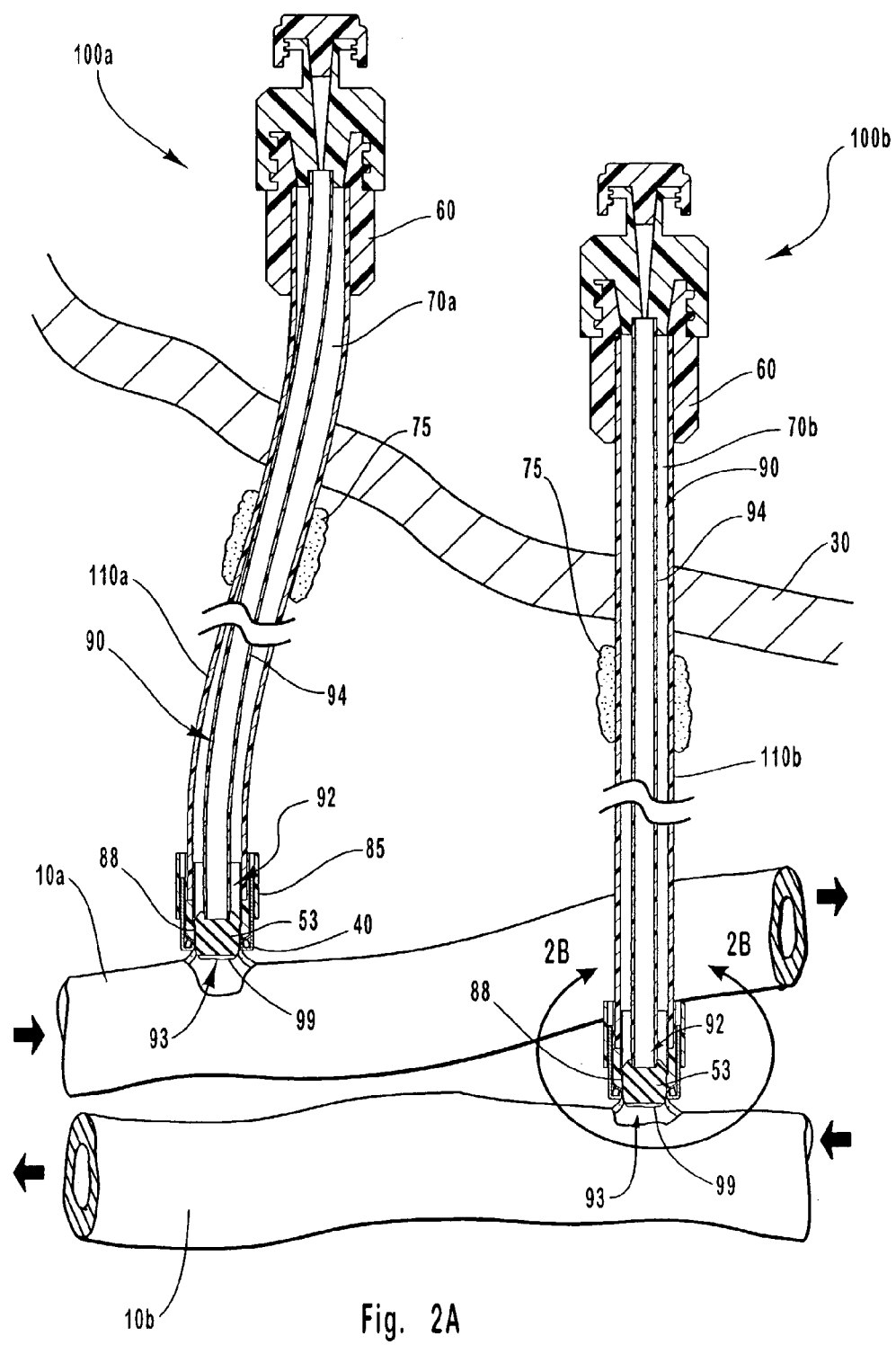
FIG. 2A is a partial cross-sectional view of the access tube devices with their occluders fully positioned inside their respective access tubes, attached to separate blood vessels, and extending through the skin.
Figure 4B:
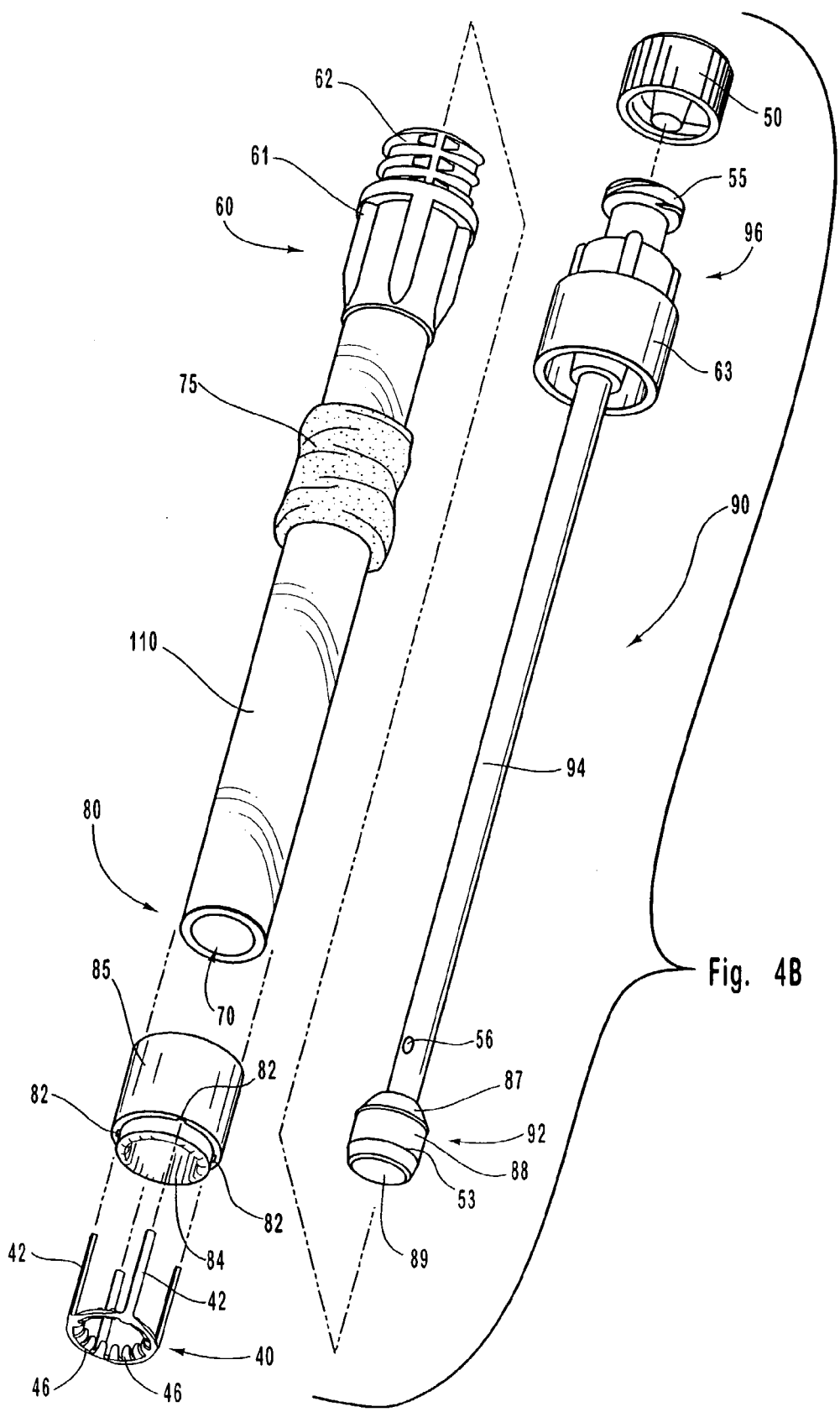
FIG. 4B is an exploded perspective view like that of FIG. 4A, but with the flushing cap and access tube anastomosis ring removed.

In FIG. 2A, each of the two access tube apparatus is shown at its anastomosis site with its respective occluder 90 in an occluding position within its respective access tube conduit 70a and 70b. The access ends 60 of the devices are seen extending through the patient's skin 30. At the occlusion ends 92 of the occluders 90 is a plug 53, which serves to seal the access tube conduit 70 from the target vessel lumen. Plug 53 typically comprises a face 89, one or more sidewalls 88, and a top surface 87, as best seen in FIGS. 4A–4B.

As can be seen in FIG. 2A, the only non-native material exposed to blood flow in the vessels comprises an exposed portion 93 of the plug 53 at the occlusion end 92 of each occluder 90. The precise surface area termed herein as exposed portion 93 will vary depending on the precise configuration of the system. Typically, however, exposed portion 93 will comprise face 89 and in some instances a portion (preferably small) of the plug sidewalls 88. "Non-native" materials, as the term is used herein, are those materials that have been introduced into the patient as part of the disclosed procedures—i.e., they are foreign materials that were not already present in the patient before introducing the access tube apparatus. Because either the entire occluder 90 or at least plug 53 at the occlusion end 92 of each occluder is replaceable, the only non-native surface area exposed to the blood stream is replaceable. This aspect of the invention helps to minimize infection, thrombosis, and other complications at the anastomosis site.

Moreover, to further reduce the incidence and likelihood of such complications, the face 89 of plug 53, or the entire plug 53, including sidewalls 88 and top surface 87, may be coated with pharmacological agents, including, but not limited to, antibacterial agents to prevent infection, antithrombotic agents to prevent thrombosis formation, and/or antiproliferative agents to prevent neo-intimal hyperplasia or other potential problems. The embodiment depicted in FIG. 2A has such a coating 99 on the face 89 and also on the sidewalls 88. A typical agent used for these coatings is an anticoagulant such as heparin or modified heparin compounds such as Duraflow II produced by Edwards Life Sciences. Antibacterial agents that have been shown to provide an effective short-term infection barrier when applied as a coating include chlorhexadine and silver sulfadiazine. Drug-eluting coatings containing antiproliferative agents, such as Paclitaxel, have been shown to be beneficial in preventing restenosis due to neo-intimal hyperplasia. However, any pharmacological substance known to those skilled in the art now or hereafter could be used as a coating.

As an alternative, some agents or substances could be integrally formed with, or otherwise incorporated into, plug 53 or a portion thereof. Applying a coating 99 on the face 89 and sidewalls 88 of the plug 53 ensures that the only surface area exposed to blood flow in the target vessels—or exposed portion 93—is not only replaceable, but also coated with agents designed to minimize the complications discussed herein. As should be apparent, any of these coatings, including antithrombotic, antiproliferative, antimicrobial coatings can be considered means for preventing complications at the anastomosis site.

Additionally, as shown by the embodiment of the access tube apparatus depicted in FIG. 5 at 100', such coatings may extend to the interior wall 72 of the access tube conduit 70. Interior wall coatings 73 may, like other disclosed coatings, may comprise pharmacological and/or antibacterial agents or, alternatively, they may comprise a lubricant or other material used to facilitate sliding the occluder 90 in and out of the access tube conduit 70. In addition, any of the various coatings discussed may be applied to other portions of the occluder 90. For instance, in an embodiment in which the interior wall 72 of the access tube conduit 70 is coated, the exterior wall of the stem 94 of the occluder 90 may also be coated with similar pharmacological and/or antibacterial agents. Again, it is possible for any of the agents discussed to be integrally formed with, rather than coated upon, any of the access tube portions discussed.

Figure 2B:
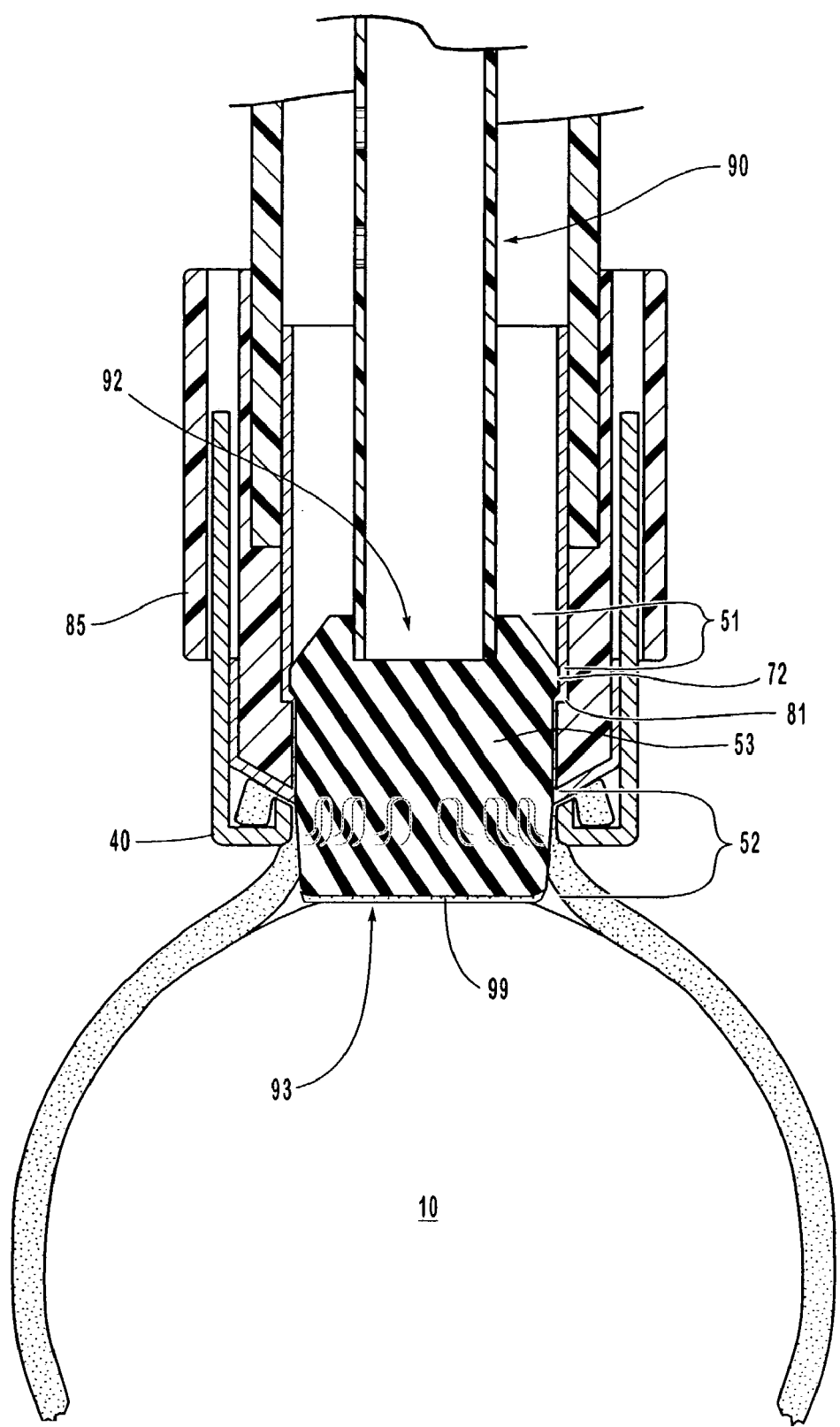
FIG. 2B is an enlarged cross-sectional view of the interface between the occlusion end of an access tube device with the occluder positioned therein and the target blood vessel wall.

FIG. 2B shows a close-up of the interface between the access tube apparatus and the target blood vessel. As indicated by the figure, plug face 89 is preferably approximately flush with the native vessel wall such that it alone comprises exposed portion 93. However, it will typically be the case that a relatively small portion of plug sidewall 88 will also comprise exposed portion 93. Still, it is desirable to provide a relatively smooth surface exposed to blood flow that is approximately flush with the vessel walls in order to reduce turbulence and other flow disturbances in the blood flow. Minimizing such disturbances is a significant factor in reducing thrombosis at the anastomosis site. Accordingly, it is preferable that when the occluder 90 is in its occluding position—i.e., it is fully inserted into the access tube lumen—plug 53 extends as far as possible through the access tube lumen but not so far that it extends significantly into the blood vessel lumen and disrupts the blood flow therein. However, due to the replaceable nature of the occluder, and in part to the optional pharmacological coatings on the exposed portion 93, the plug face 89 does not necessarily need to be flush with the vessel wall. In other words, because other aspects of the invention serve to control potential complications at the anastomosis site, embodiments wherein plug 53 extends into the vessel lumen or wherein the plug face 89 sits recessed or extended from the vessel wall are within the scope of the present invention.

Figure 2C:
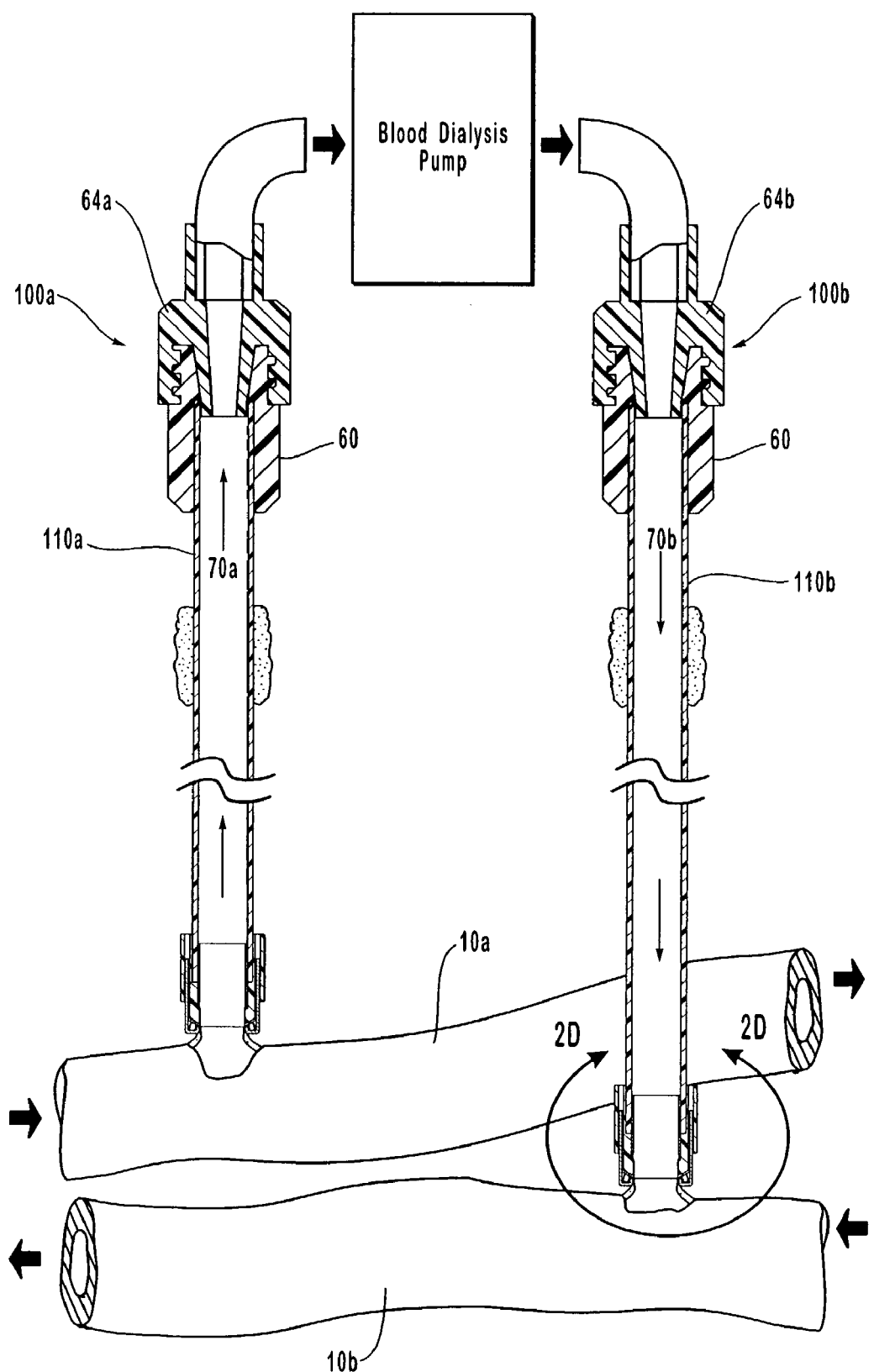
FIG. 2C is a partial cross-sectional view like that of FIG. 2A, but with the occluders withdrawn for blood treatment.
Figure 2D:
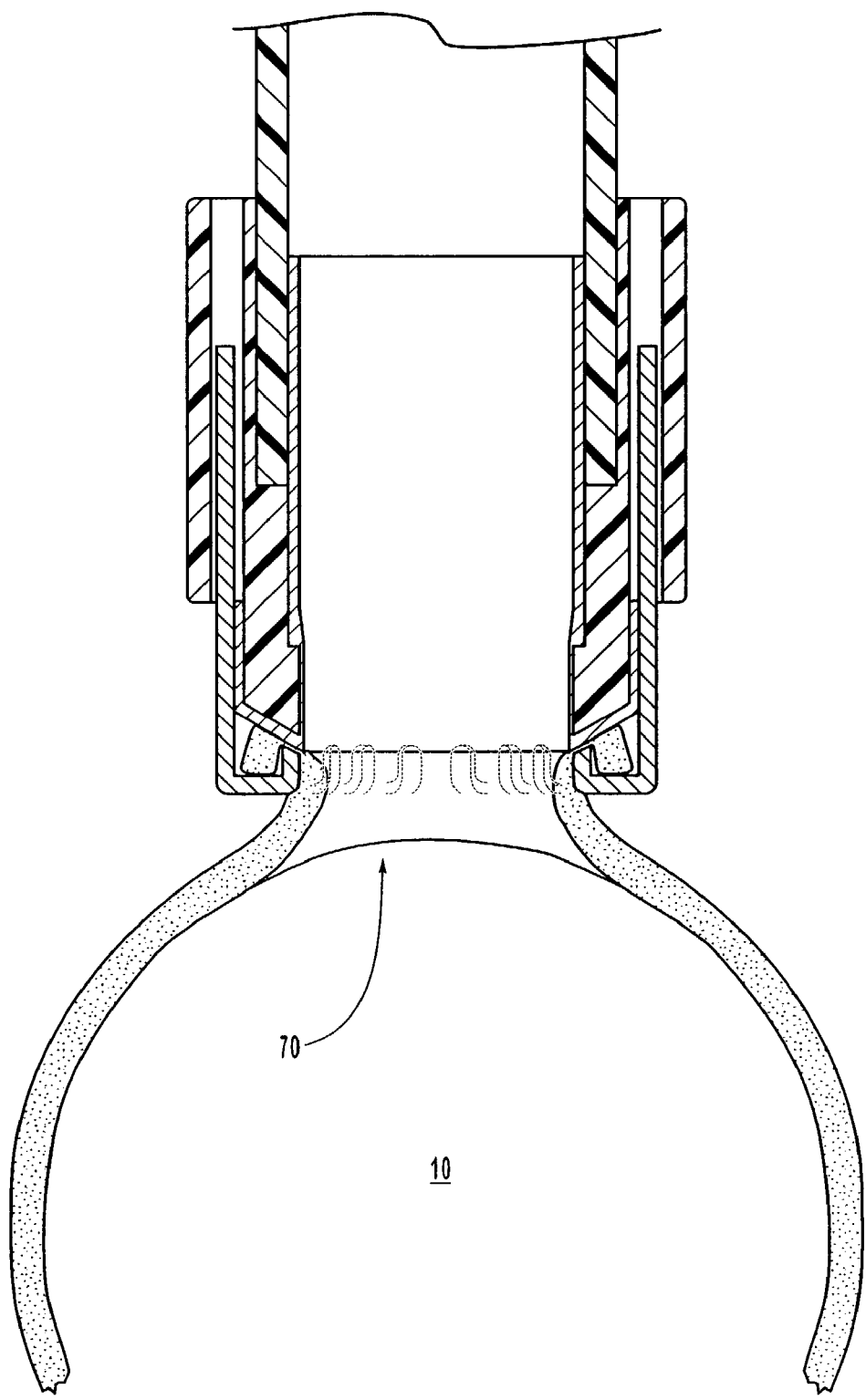
FIG. 2D is an enlarged cross-sectional view like that of FIG. 2B, but with the occluder withdrawn.

In FIG. 2C the access tubes are shown with their occluders removed to allow for vascular access for blood treatment. As the arrows in the figure indicate, blood flows from blood vessel 10*a* into the access tube conduit 70*a* of occludable extraction access tube apparatus 100*a* and is drawn to a blood treatment device. The blood treatment device is most typically a hemodialysis machine, but it can be any device capable of performing blood treatment of any kind outside a patient's body. After the blood has been treated, it is inserted into blood vessel 10*b* via the access tube conduit 70*b* of occludable insertion access tube apparatus 100*b*. Typically, and as shown in FIG. 2C, the access ends 60*a* and 60*b* of the devices are adapted to be fitted with corresponding port devices 64*a* and 64*b* during blood treatment, which are adapted to be fitted on their opposing ends to the blood treatment device.

Referring now to FIG. 3, the extraction access tube apparatus 100*a* is anastomosed to blood vessel 10, and the insertion access tube apparatus 100*b* is anastomosed to the same blood vessel 10 at a downstream location. Otherwise, the embodiment shown in FIG. 3 is identical to that shown in FIGS. 2A–B. Again, as indicated by the arrows, blood from blood vessel 10 is drawn through access tube conduit 70*a* and into a blood treatment device, after which it is re-inserted into blood vessel 10 through access tube conduit 70*b*.

FIGS. 4A–4B provide a more detailed depiction of the embodiment of the access tube apparatus of the present invention shown in FIGS. 1–3 with occluder 90 withdrawn from access tube conduit 70. Access tube 110 has an anastomosis end 80 opposite from an access end 60. A conduit 70 extends from the anastomosis end 80 to the access end 60. The access tube 110 and conduit 70 therein can be of any cross-sectional shape and size. Moreover, the term "access tube" is meant to encompass any of various known or hereafter known suitable devices, including graft vessels, catheters, and the like. These are all also examples of access tube means for accessing an anastomosed vessel. An access tube has an anastomosis end adapted for attachment to the sidewall of a vessel if it is suitable for attachment there. An anastomosis component, such as an anastomosis ring, plates, etc., can facilitate the attachment, or the access tube can have preformed holes at the anastomosis end for suturing. Another example of an access tube with an anastomosis end adapted for attachment to the sidewall of a vessel is an access tube that is soft enough to be punctured by standard suturing procedures, such as a graft vessel. The portion of the access tube defining the conduit 70 is typically made of a flexible and blood-compatible material, such as polyurethane or silicone. However, it could be made of any other blood-compatible material.

Although not necessary, using a flexible material to form the portion of access tube 110 defining the conduit 70 may be desirable for a number of reasons. As discussed earlier, providing a flexible access tube allows the percutaneous portion of the tube to be flexed and pressed against the skin, perhaps even affixed to the skin, when not in use. This contributes to the inconspicuousness of the device and for that reason alone may be desirable from a patient's perspective. It also may assist in keeping the percutaneous portion of the device from being pulled or otherwise disturbed by the patient and his surroundings while conducting everyday activities, and further may prevent or at least mitigate injury to the patient when the device is inadvertently bumped against external objects. If desired, the access tube may also be formed from more than one material. For instance, the portion of the access tube that is to remain in a subcutaneous position may be made of a more rigid material, while the portion that is to remain in an extracorporeally accessible position may be made of a more flexible material. In such an embodiment, cuff 75 (discussed later) could serve as the interface between the subcutaneous material and the percutaneous material. Or, to achieve a similar configuration, the subcutaneous portion could have a greater wall thickness than the portion that is to remain extracorporeally accessible.

When made from a flexible material, the access tube can be positioned such that it protrudes from the skin at a location remote from the anastomosis site. In such embodiments, the access tube is inserted into the skin at a desired location and then routed underneath the skin to a desired target vessel. This allows the access end 60 of the access tube to be positioned at a safe and comfortable location as desired.

Conduit 70 of the access tube may also be tapered such that it has a circumference at the anastomosis end that is smaller than the circumference of the conduit at the control end. Such a configuration may assist in making a fluid-tight seal at the anastomosis site.

The access end 60 of the access tube has a cap base 61 for engaging an access cap 63 of the occluder 90. The cap base may comprise any configuration suitable for engaging a portion of the occluder 90—preferably an access cap 63—to keep the occluder 90 within the access tube conduit 70 and prevent the occluder 90 from being inadvertently withdrawn. To achieve this, cap base 61 may be configured to allow for a snap-fit, threaded, friction-fit or other suitable junction between it and the access cap 63. As shown in FIGS. 4A–4B, some embodiments utilize threads 62 to threadably engage access cap 63.

As shown in FIGS. 4A–4B, the anastomosis end 80 of the access tube has an access tube anastomosis ring 85 adapted to cooperate with a target vessel anastomosis ring 40. Access tube anastomosis ring 85 is an example of a component of an anastomosis device that is attached to the access tube. The access tube anastomosis ring 85 may also be configured to be integral with the access tube. Any anastomosis components known to those of skill in the art that can be used to join vessels together with an access tube are within the scope of the present invention. For example, the anastomosis component at end of the access tube may have holes that have been preformed to facilitate suturing the access tube to a target vessel. Alternatively, as previously discussed, an anastomosis component need not be a part of the device at all. The access tube may simply be sutured directly to the target vessel wall, or be attached thereto by any other suitable method. An access tube that is soft enough to be punctured by suturing procedures, such as a graft vessel, is an example of an access tube with an anastomosis end adapted for attachment to the sidewall of a vessel that lacks an anastomosis component.

The target vessel anastomosis ring 40 preferably has posts 42 that are insertable into post slots 82, which are formed in access tube anastomosis ring 85. Preferably, the posts 42 fit inside the post slots 82 such that they are frictionally retained by the post slots 82. Accordingly, once the everted target vessel wall has been placed onto target vessel anastomosis ring 40, as discussed in greater detail later, the anastomosis end 80 of the access tube can be drawn closer to the anastomosis site and its position there can be frictionally maintained by driving the posts 42 further into the slots 82. Various other mechanisms can be used to hold the rings together, such as those disclosed in U.S. patent application Ser. No. 09/736,937 titled Locking Compression Plate Apparatus, which was filed on Dec. 14, 2000, the disclosure of which is expressly incorporated herein by reference.

As indicated above, the access tube anastomosis ring 85 containing the slots 82 can be integrally formed with access tube 110 or it can be attached to access tube 110 by using any suitable attachment means, including any of various mechanical or medical bonding techniques. The access tube anastomosis ring 85 can be made of a variety of flexible, blood-compatible materials, such as polyurethane and the like. However, for reasons discussed below, access tube anastomosis ring 85 will typically be made of a less flexible material than that used to form the portion of access tube 110 defining the conduit 70.

Access tube anastomosis ring 85 and target vessel anastomosis ring 40 are both examples of means for facilitating anastomosis of access tube means to an anatomical vessel. Several other examples of such means are disclosed herein. For instance, an anastomosis component having preformed holes for suturing, an anastomosis plate, or any other anastomosis component known to those of skill in the art, or hereafter known, that can be used to join a vessel together with an access tube are examples of means for facilitating anastomosis. Embodiments of the access tube apparatus 100 can utilize one such means, more than one such means, or none at all.

Also, the target vessel anastomosis ring 40 preferably has holding tabs 46 extending towards the access tube or away from the target blood vessel. As discussed in greater detail later, the holding tabs 46 facilitate holding the perimeter of an opening in the target vessel wall in an everted position. Moreover, these holding tabs may be adapted to interdigitate to some degree with access tube holding tabs 86, which may be attached to or preferably integrally formed with the access tube anastomosis ring 85.

Figure 4C:
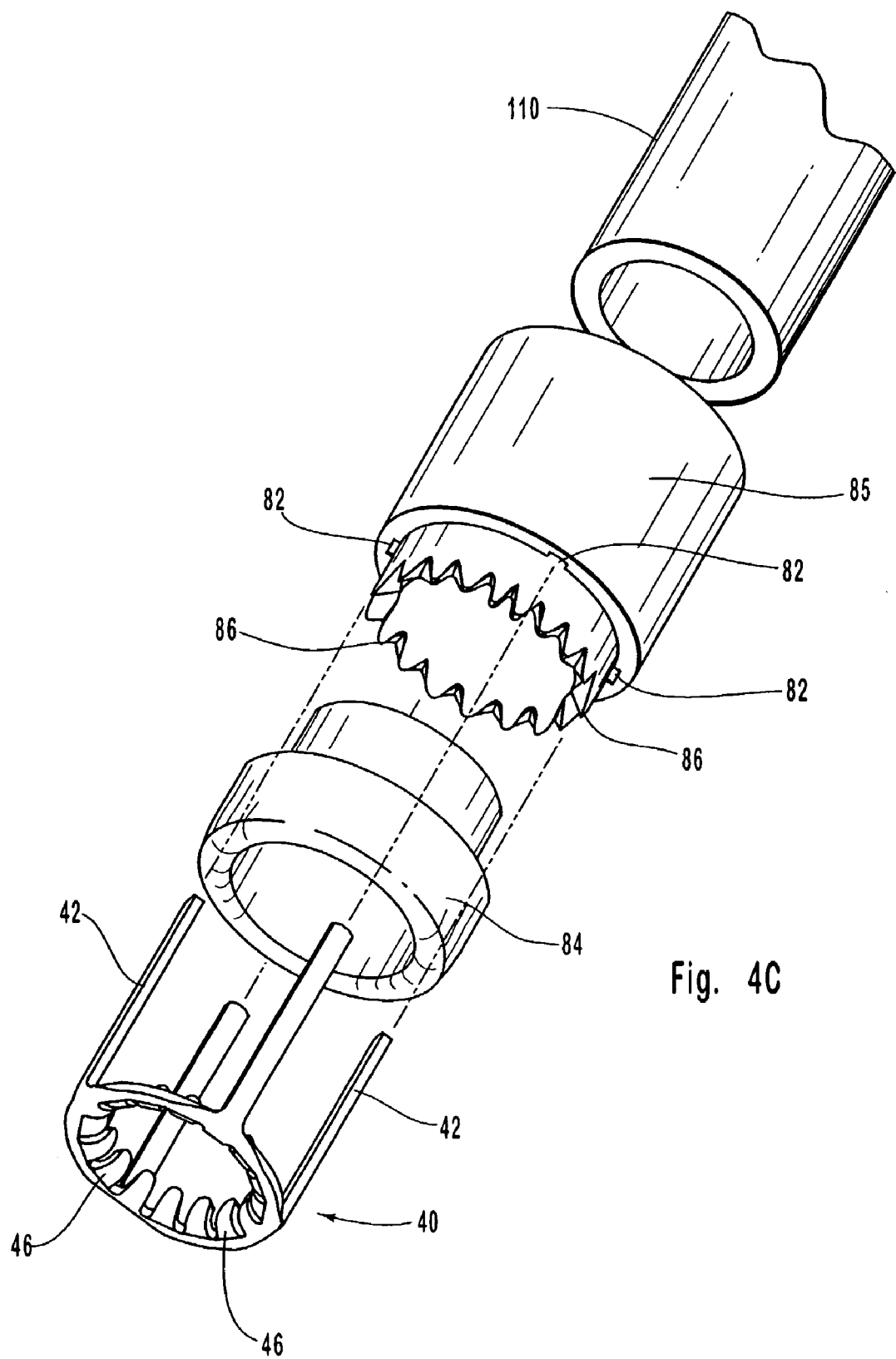
FIG. 4C is an enlarged, exploded perspective view of the anastomosis end of the device like that of FIG. 4B, but with the covering shown removed from the access tube anastomosis ring and exposing the access tube holding tabs.

Access tube holding tabs 86, along with a portion of the interior surface 72 of access tube conduit 70, may optionally be covered with a covering 84, as shown in FIGS. 4A–4B and as shown separated from access tube holding tabs 86 in FIG. 4C. This covering is preferably made of a porous expanded polytetrafluoroethylene (ePTFE) or a material with similar properties, but could also be made from a variety of other materials. Still, any such material will typically be porous and allow for in-growth of biological tissue. In addition to providing a base for tissue in-growth, such a covering provides some cushion for forming a liquid-tight seal at the anastomosis end, and moreover allows the anvil apparatus (discussed later) to center itself more easily on access tube anastomosis ring 85.

A portion of the access tube may be covered with a bio-compatible cuff 75, as best seen in FIG. 2A. The cuff 75 is typically placed on the access tube such that it is located just under the patient's skin 30. When so positioned, fibrous tissue can grow into the cuff 75 such that it integrates with the patient's body and serves as a mechanical anchor to the access tube. Cuff 75 could alternatively be placed at the skin layer 30. Cuff 75 also serves as a transcutaneous infection barrier. In one embodiment, the cuff 75 is made from a polyester felt, but any suitable bio-compatible material could be used.

Fitting within the conduit 70 of the access tube is an occluder 90. The occluder 90 is best seen in FIGS. 4A–4B, which show it removed from the access tube conduit 70. Occluder 90 has an occlusion end 92 opposite from a control end 96. The main components of occluder 90 include a plug 53 at occlusion end 92, an access cap 63 at control end 96, and a stem 94 extending from plug 53 to access cap 63. As seen from the figures, stem 94 has a smaller diameter than plug 53.

As shown in FIGS. 4A–4B, plug 53 comprises a face 89, one or more sidewalls 88, and a top surface 87. Plug 53 serves to form a seal at anastomosis end 80 of the access tube 110. In addition, plug 53 serves to seat the occluder 90 within the access tube conduit 70 in its proper occluding position, and further plug 53 serves to form an internal seal used to allow fluids to be introduced into the conduit 70 from the access end, as discussed later. Face 89 will typically be flat, but can also have various different shapes. For instance, face 89 could be concave or convex.

The various portions of occluder 90 can be made from a variety of suitable materials. The following are illustrative examples of suitable materials, but should not be considered limiting.

Plug 53 can be made of materials such as polyvinylchloride, polyurethane, silicone, or any other suitable blood-compatible material. It may also consist of a substrate made of such a material that is coated with one or more pharmacological agents, such as heparin or heparin-based antimicrobial or antiproliferative agents. For example, in one embodiment the occlusion end 92 is made using a polyvinylchloride substrate coated with a polyurethane mixture having a heparin-based pharmacological agent incorporated therein. As further alternatives, the agents could be integrally formed with the substrate, and/or a polymer could be added to the coating to control the rate of elution.

Stem 94 can be made of similar materials such as polyurethane, or it can be made of any other suitable material such as other plastics or metals. The access cap 63, along with the cap base 61 of the access tube can be made of any blood-compatible material. In one embodiment, the access cap 63 and mating cap base 61 are made of acrylonitrile butadiene styrene (ABS).

Figures 4D, 4E:
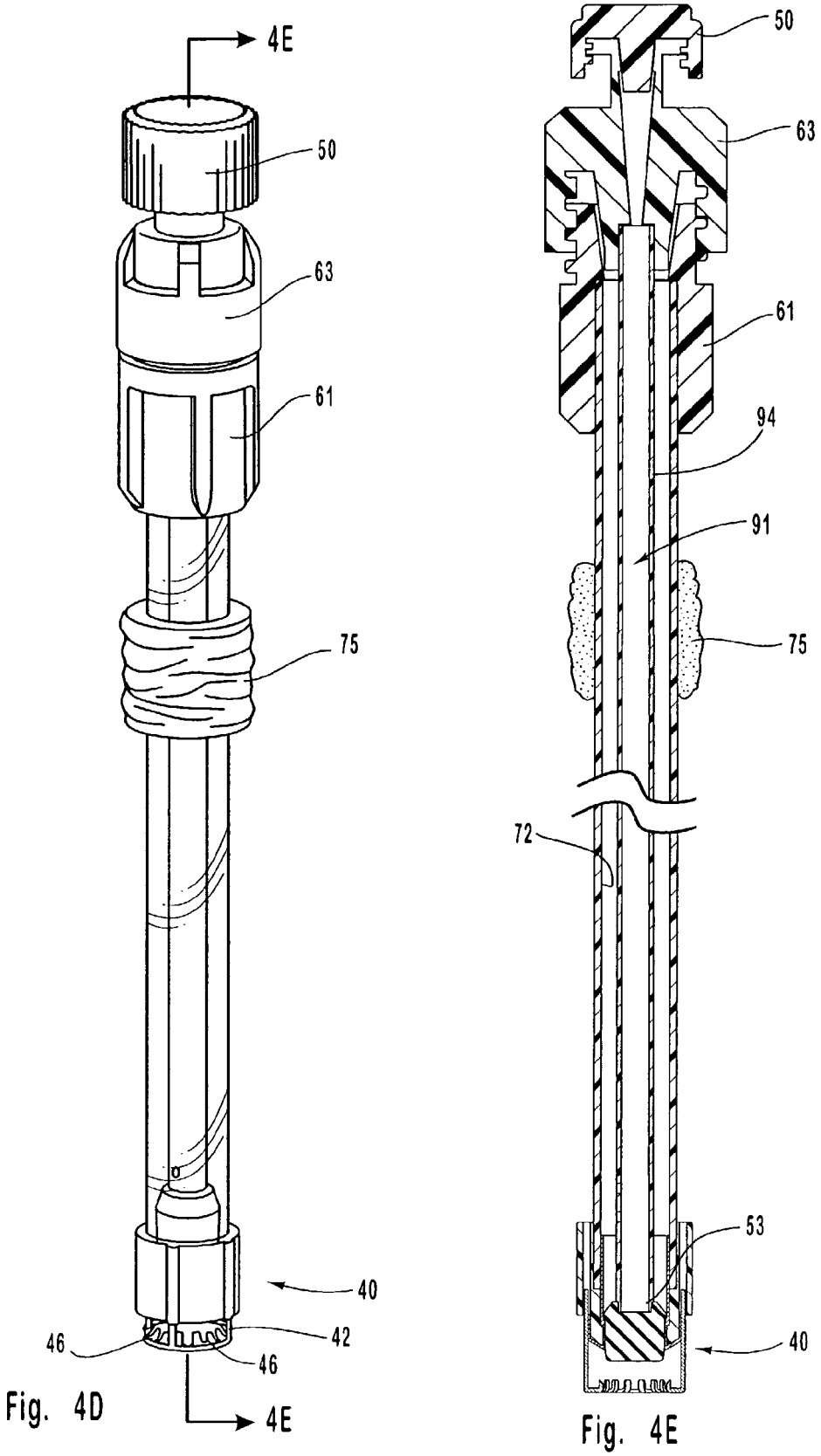
FIG. 4D is a perspective view of the access tube device by itself and with the occluder inside.
FIG. 4E is a cross-sectional view of the access tube device shown in FIG. 4D.
Figure 4F:
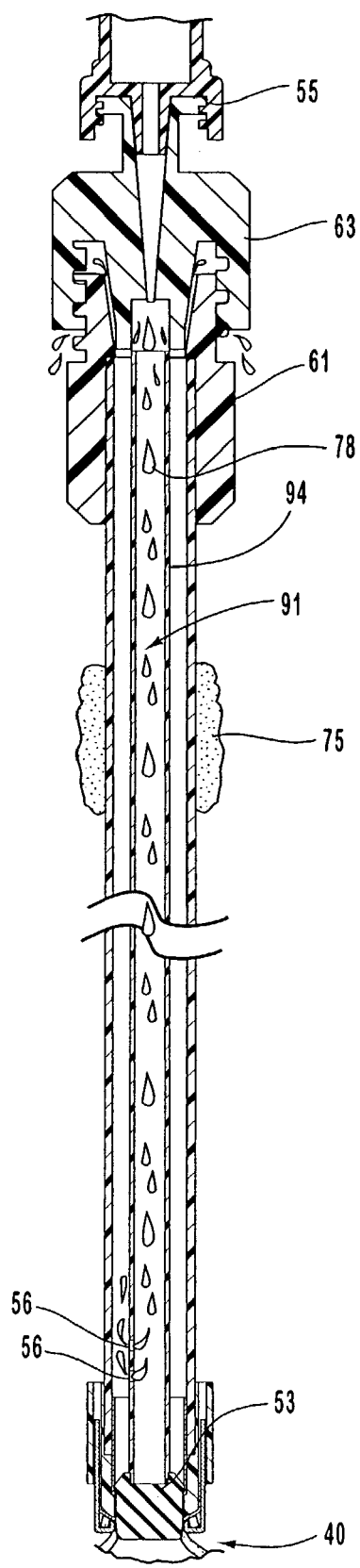
FIG. 4F is a cross-sectional view showing the flushing cap removed and flushing fluid introduced through the flushing conduit and into the chamber.

As best seen in FIGS. 4E–4F, a flushing conduit 91 may run down the center of stem 94. The flushing conduit 91 extends from one or more pores 56 to an opening or port 55 at the cap end 96 of the occluder to provide fluid communication between port 55 and pore(s) 56. The port 55 may be selectively blocked at the cap end 96 with a flushing cap 50, which is threadably engagable with the port end 55 of the flushing conduit 91. Of course, flushing cap 50 need not be threaded. Any suitable configuration for keeping flushing cap 50 in place may be used. Like other parts of the device, the flushing cap 50 may be made of a variety of plastics or other suitable materials. The function of the flushing conduit 91 and related aspects of the present invention are discussed in greater detail later.

If the portion of the access tube defining the conduit 70 is flexible, as previously discussed, part of plug 53 of the occluder 90 can be slightly larger in diameter than the diameter of the interior wall 72 of the access tube conduit 70. In such an embodiment, the access tube conduit 70 bulges slightly as this portion of plug 53 passes therethrough. This creates a seal between the access tube conduit and the vessel lumen. For instance, a sealing lip 72 can be formed in plug 53 of the occluder 90, as seen in FIG. 2B. The sealing lip 72 is a narrow circumferential ridge that causes the access tube conduit 70 to bulge out when the occluder 90 is inside the conduit 70, thereby providing a tight seal against the interior wall 72. The seal caused by sealing lip 72 prevents fluid introduced through the flushing conduit 91 from leaking past plug 53 and into the target vessel lumen. This seal also acts as an additional barrier to prevent the blood or other body fluid from entering the access tube conduit 70.

Moreover, sealing lip 72 may be used to seat the plug 53 in its occluding position. In other words, it can be used as a ledge to engage another portion of the access tube device in order to seat the plug 53 in a desired occluding position by preventing it from going past that position. There are a variety of options for engaging the sealing lip 72. For example, covering 84 may be used to engage sealing lip 72. Alternatively, access tube 110 or access tube anastomosis ring 85 can be formed with a ledge 81, as also shown in FIG. 2B, which is configured to engage sealing lip 72.

Plug 53 may also have one or more tapered portions. The plug embodiment depicted in FIG. 2B has a first tapered portion 51 extending from the distal end of stem 94 to sealing portion 54. In this embodiment, the portion of plug 53 extending beyond access tube anastomosis ring 85 is also tapered. This tapered portion 52 is tapered in order to facilitate seating the occluder against the everted target vessel tissue and also to help prevent damage to the vessel tissue which might otherwise be caused during the process of seating the plug in its occluding position.

It should be understood that many variations of the shape of the plug 53 are within the scope of the present invention. For instance, plug 53 may have fewer or more tapered portions, or it need not be tapered at all. An example of an additional taper would be a seating tapered portion. A seating tapered portion may be used to position plug 53 at its proper occluding position. It could be used to seat plug 53 onto the end of covering 84. Alternatively, such a seating tapered portion could seat itself onto a protrusion or mating tapered portion formed in access tube anastomosis ring 85, as discussed above.

Because access tube anastomosis ring 85 is typically made of a less flexible material than that of the portion of access tube 110 defining the conduit 70, sealing portion 54 of plug 53 is prevented from extending into access tube anastomosis ring 85. Again, this feature, along with tapered portion 57 extending from sealing portion 54, facilitate positioning and seating the occluder in its occluding position and prevent it from extending too far into the target vessel.

It should be understood that the shape of the occluder does not limit the scope of the present invention. While the embodiment discussed thus far utilizes a stemmed occluder wherein only the plug 53 of the occlusion end 92 fits tightly within the access tube conduit 70, countless other variations on the shape and size of the occluder and access tube are possible. To illustrate one such possible variation, refer to FIG. 5. FIG. 5 shows an embodiment 100' of the access tube device having a uniformly-shaped occluder. In other words, when the occluder is inside the access tube conduit 70, the occluder fits tightly against the interior wall 72 of the access tube conduit along the entire length of the portion of the occluder that fits within the access tube conduit 70.

It should also be understood that various other embodiments within the scope of the present invention are possible. For instance, two separate access tubes need not be used. Instead, blood can be extracted from and inserted into the same access tube, either simultaneously in a dual-lumen access tube, or intermittently. In addition, only one access tube would be needed for other uses, such as withdrawing particularized amounts of blood for testing, inserting medications or other pharmacological agents into a patient's blood stream, etc.

Figure 6:
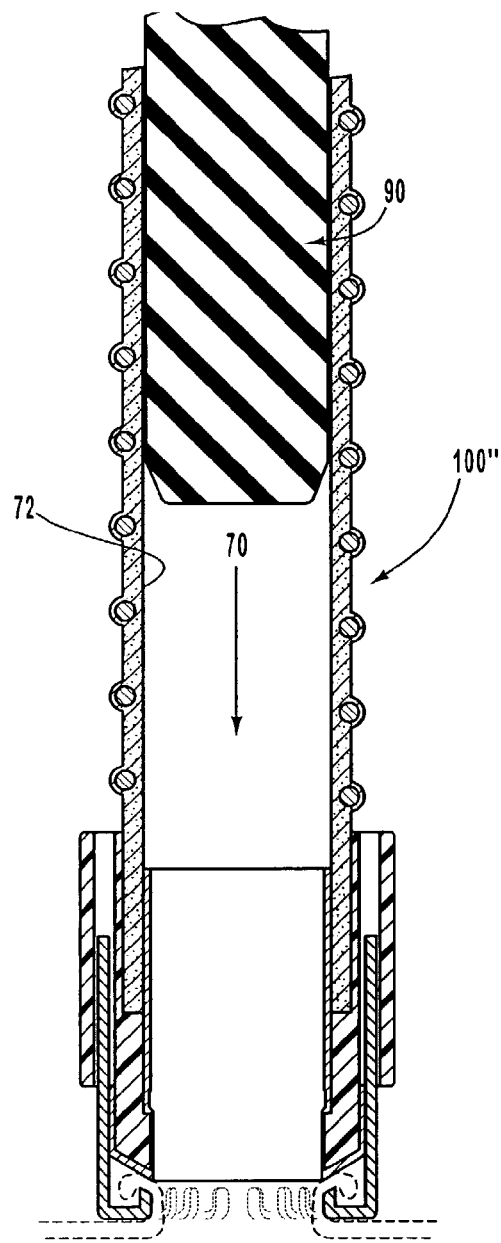
FIG. 6 is a cross-sectional view of an embodiment of the device wherein the access tube is a graft vessel and employing a uniformly-shaped occluder without a coating.

Moreover, as previously discussed, the access tube of the present invention can comprise any of the various known or hereafter known tubular devices, such as graft vessels, catheters, etc. For example, FIG. 6 shows a graft vessel employed as the access tube of the present invention. Although not shown in the figure, the access end of the graft vessel access tube can be fitted with an access cap such as disclosed herein, or it can be fitted with any other such cap that serves the same purposes. It should be apparent that FIG. 6 is but one additional example, and that many additional variations are possible, each of which remains within the scope of the invention.

As discussed above, access end 60 of access tube 110 may have threads 62 to engage with access cap 63. Threads 62 may also be used to engage a port device 64, as shown in FIG. 2C and FIG. 3. As discussed earlier, the cap base need not include threads. Any configuration designed to secure the access cap 63 of the occluder 90 to the access tube is within the scope of the invention.

When the access cap 63 of this embodiment is engaged with the access end 60 of the access tube 110, making a seal between the occlusion end 92 of the occluder 90 and the interior wall 72 of the access tube conduit 70 creates a chamber 71, which is best seen in FIG. 4E. This chamber is defined by the interior wall 72 of the conduit 70, the exterior wall of the stem 94 of the occluder 90, the occlusion end 92 or plug 53 of the occluder 90, and the access cap 63 of the occluder 90. The advantages achieved by providing a chamber 71 are discussed below.

During treatment, the conduit of the access tube is exposed to blood from the vessel, and may also be exposed to bacteria or other harmful materials from the environment around the access end 60. Such materials may have a tendency to accumulate on the interior wall 72 of the conduit 70. To eliminate or at least ameliorate such problems, one embodiment of the present invention allows for a fluid 78—preferably an antibacterial fluid—to be introduced into the chamber 71 to flush out and/or sanitize the access tube conduit 70. As shown in FIG. 4F, such a fluid 78 may be introduced at the access end of the access tube via a port 55 at the cap end 96 of the occluder 90. Typically, access cap 63 is disengaged from access end 60 of access tube 110 during the flushing, so as to allow the flushing fluid to exit chamber 71.

The port 55 is covered with a flushing cap 50 when not in use. The flushing cap 50 may be engaged to port 55 by any suitable means, including threads, snap-fit, friction-fit, etc. As shown in FIG. 4F, one embodiment provides for a threaded engagement between the flushing cap 50 and port 55. Once removed, the flushing cap 50 reveals a flushing conduit 91 defined by the stem 94 of the occluder 90. The flushing conduit 91 opens at one or more pores 56. Pore 56 allows the fluid to enter the chamber 71 to flush and/or sanitize the access tube. Flushing fluid 78 may be flushed through chamber 71 and then out of access end 60 or it may be left in chamber 71 between treatments.

Chamber 71, which allows for flushing the conduit of the access tube, is one example of a means for preventing infection in the access tube means. Another example of such means is providing for one or more coatings inside the access tube means conduit.

One method for anastomosing the access tube apparatus 100 to the sidewall of a blood vessel is carried out by using an anvil apparatus 200, which includes an anvil 210 and an anvil pull 230, and an external anastomosis operator 700. Briefly stated, the anastomosis operator 700 functions to make an incision or access hole in the sidewall of a target vessel 10 at an anastomosis site and anastomose the access tube of the present invention to the target vessel at the access hole. The operator 700 utilizes an anvil apparatus 200, best seen in FIGS. 7A–7D, that facilitates making the opening in the target vessel wall 10. Anvil apparatus 200 may be intraluminally directed within the vessel to the anastomosis site or it may be externally positioned into the lumen at the anastomosis site.

More detailed information regarding methods for intraluminally directing an anvil apparatus is provided in U.S. patent application Ser. No. 09/736,839 titled "Intraluminally Directed Anvil Apparatus and Related Methods and Systems" and filed on Dec. 14, 2000, which is hereby expressly incorporated by reference. Also, more detailed information regarding methods for externally positioning an anvil apparatus is provided in U.S. patent application Ser. No. 10/003, 956 titled "Externally Positioned Anvil Apparatus for Cutting Anastomosis" and filed on Oct. 31, 2001, which is also hereby incorporated by reference.

As seen sequentially in FIGS. 7A–7F, a cutter 400 (discussed in greater detail later) engages anvil 210 of anvil apparatus 200, thereby forming an opening in the target vessel wall. Anvil apparatus 200, used in connection with the operator 700, also facilitates everting the vessel tissue defining the opening over the holding tabs 46 of the target vessel anastomosis ring 40. The operator 700 then is used to draw the posts 42 of the target vessel anastomosis ring into the post slots 82 of the access tube anastomosis ring 85, which completes the anastomosis procedure. Of course, after the anastomosis procedure has been completed, the occluder 90 is inserted into the access tube conduit 70 to maintain blood flow control at the anastomosis site.

Figure 7A:
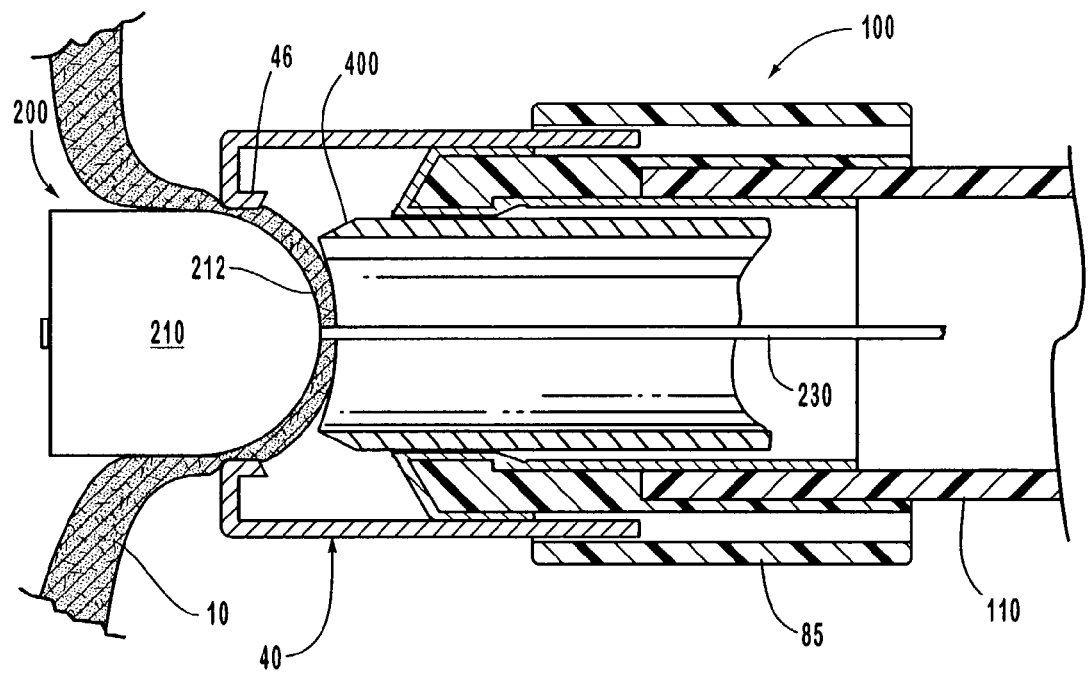
FIG. 7A is an enlarged cross-sectional view of the anvil apparatus distending the target vessel wall and the cutter of the external anastomosis operator being drawn towards the anvil apparatus.

FIG. 7A depicts anvil 210 being pulled into the target vessel anastomosis ring 40 and against the intima or interior wall of the target vessel 10. Also shown is cutter 400 extending through access tube 110 and approaching distended target vessel 10 on anvil 210.

Figure 7B:
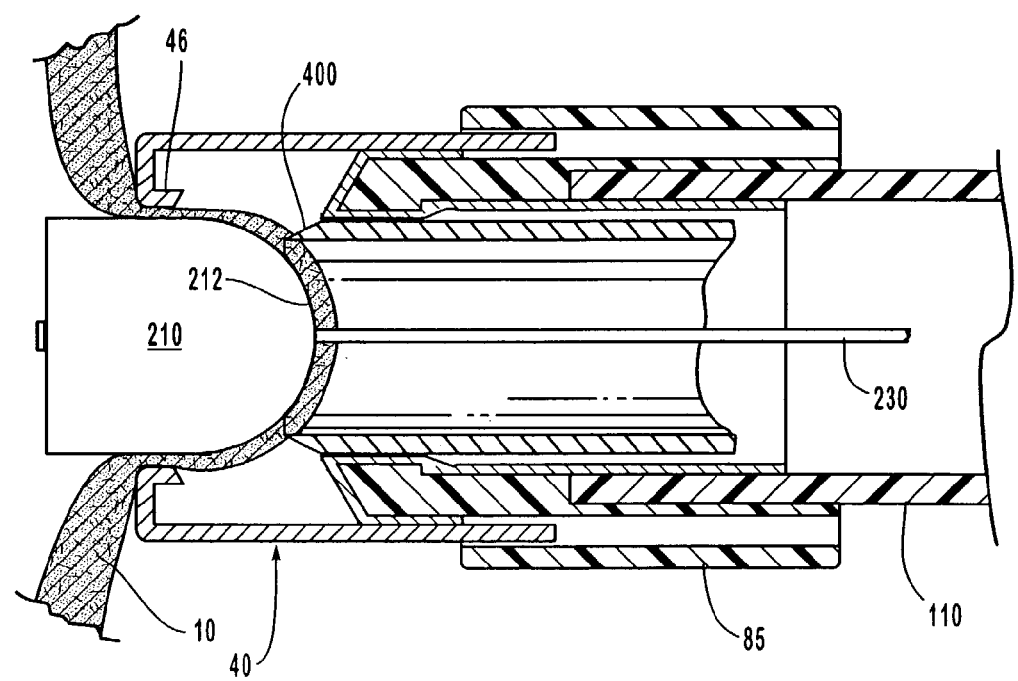
FIG. 7B is an enlarged cross-sectional view like that of FIG. 7A after the cutter has engaged the anvil apparatus to cut the target vessel wall and evert the target vessel tissue over the holding tabs.
Figure 7C:
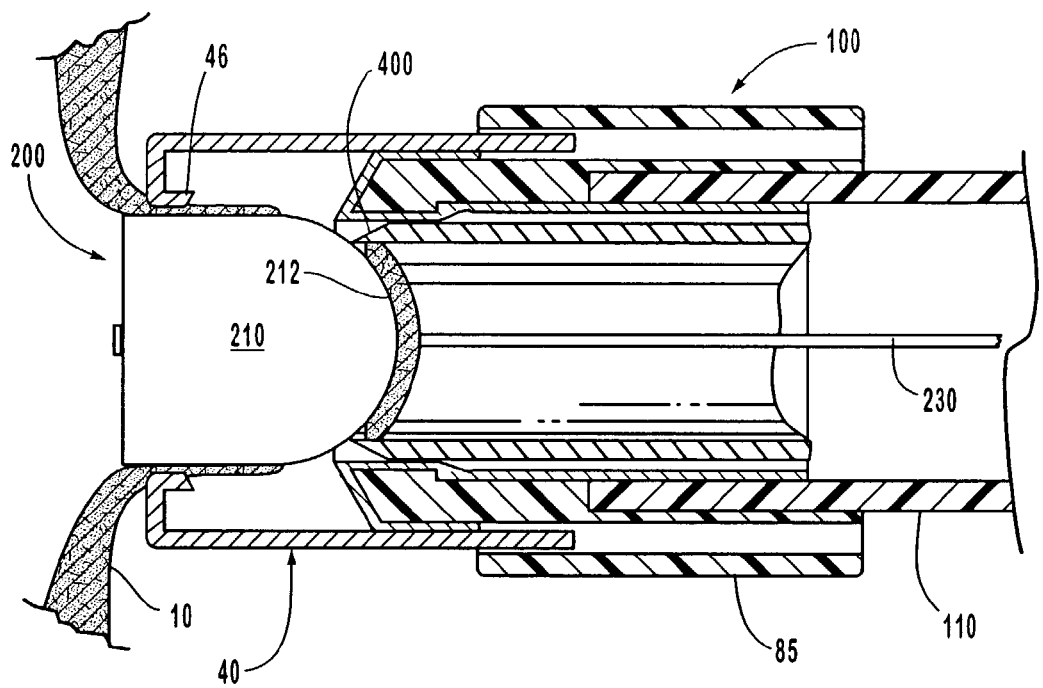
FIG. 7C is an enlarged cross-sectional view like that of FIG. 7B after the cutter has cut the target vessel wall, showing the target vessel tissue in a position to be everted over the holding tabs.

FIG. 7B depicts the formation of a target vessel opening in the wall of the target vessel 10. This opening is formed by pulling the anvil 210 towards cutter 400 such that cutter 400 engages the vessel wall. As shown in FIG. 7C, cutter 400 also engages anvil 210 so as to ensure a clean cut of the vessel wall. After the cut has been made, the portion of the target vessel wall that now defines the opening rests on the side or landing of anvil 210. This landing aids in everting the tissue that is to be anastomosed as a section of the tissue is held between the landing and holding tabs 46 with a length of tissue resting on the landing that is sufficient to be everted onto holding tabs 46.

Figure 7D:
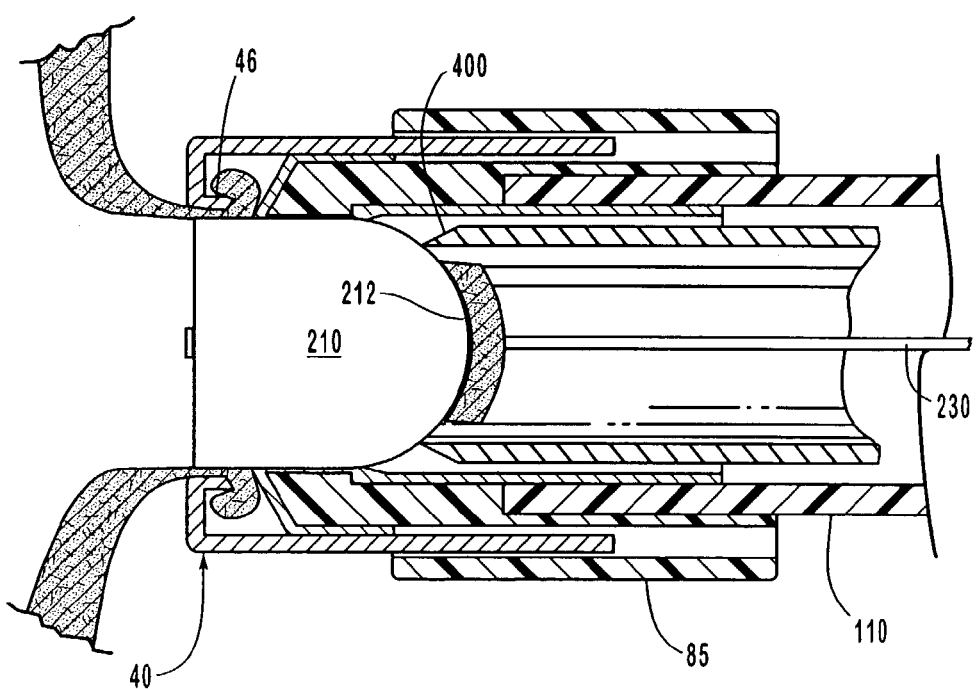
FIG. 7D is an enlarged cross-sectional view like that of FIG. 7C after the target vessel anastomosis ring has been drawn towards the access tube anastomosis ring to complete the anastomosis procedure.
Figure 7E:
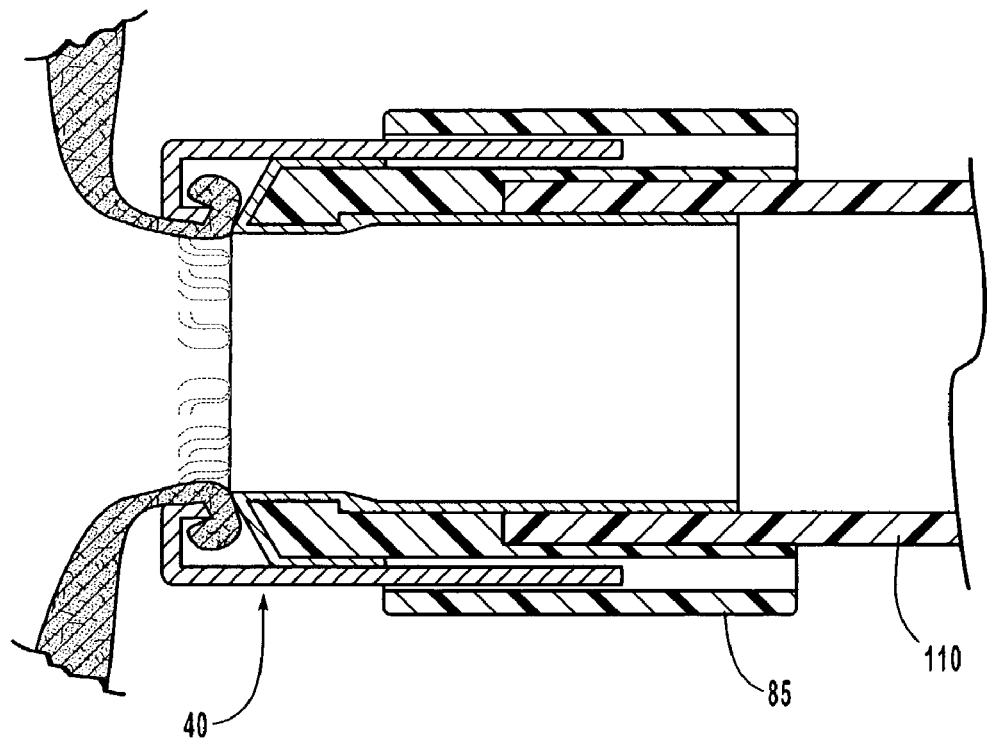
FIG. 7E is an enlarged cross-sectional view like that of FIG. 7D after the cutter and anvil apparatus have been withdrawn through the access tube conduit and the anastomosis procedure has been completed.
Figure 7F:
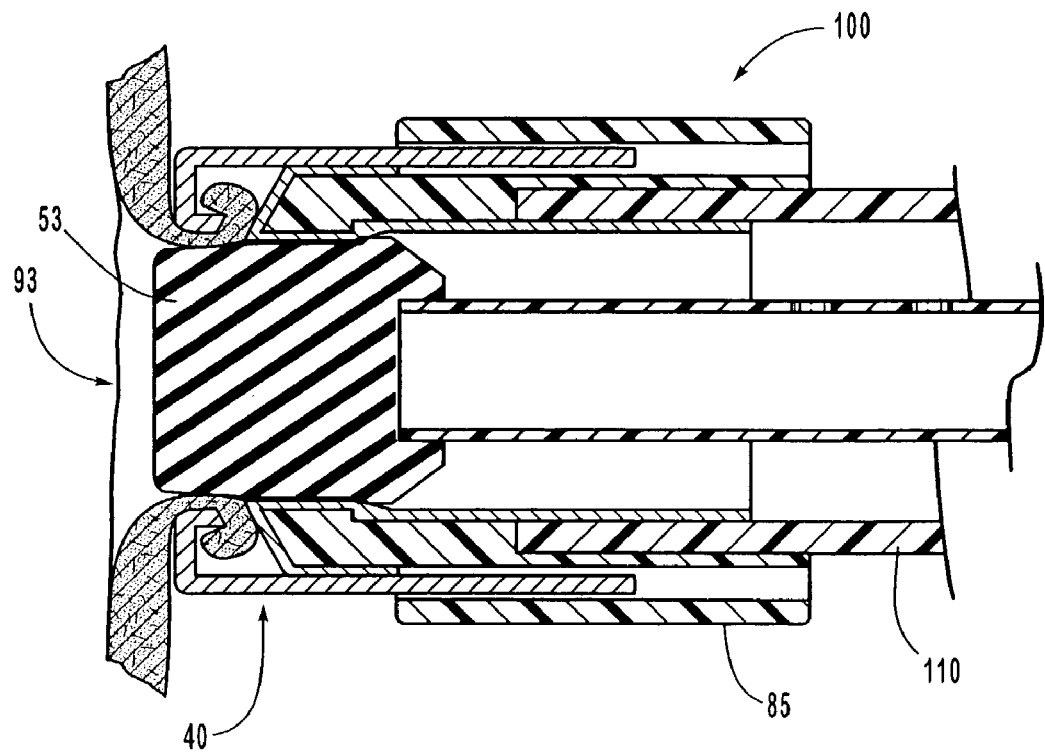
FIG. 7F is an enlarged cross-sectional view like that of FIG. 7E after the occluder has been fully positioned inside the access tube.

As shown in FIG. 7D, access tube anastomosis ring 85 is then brought together with target vessel anastomosis ring 40. In doing so, holding tabs 46 with the everted tissue held thereon are approximated with holding tabs 86 on the access tube anastomosis ring 85. This will typically allow the tissue to interdigitate to some degree with covering 84 on holding tabs 86. Once the anastomosis is completed, cutter 400 and anvil 210 are drawn through the access tube conduit 70 and out of access tube 110, such that conduit 70 is open as shown in FIG. 7E. Finally, as shown in FIG. 7F, the occluder 90 is inserted into access tube conduit 70 to block fluid communication between the target vessel 10 and the conduit 70.

The external anastomosis operator 700, which is used to carry out the steps depicted in FIGS. 7A–7E, will now be described in greater detail. It should be understood, however, that although the following anastomosis method is disclosed in detail, many variations are possible, each of which remains within the scope of the present invention.

Figure 8A:
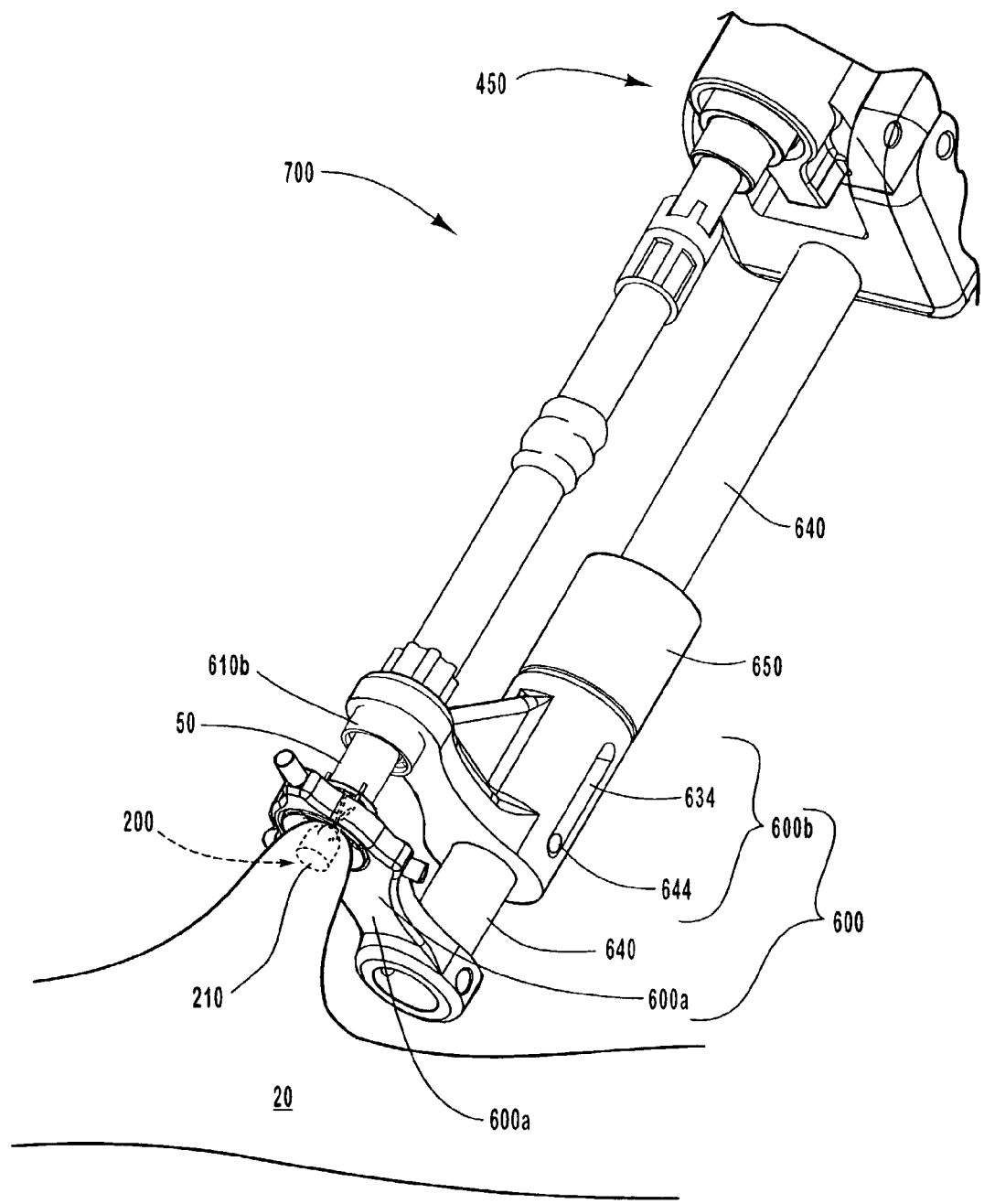
FIG. 8A is a perspective view of the external anastomosis operator engaging the anvil apparatus inside the target blood vessel during an anastomosis procedure.

FIG. 8A shows the external anastomosis operator 700 with an attachment actuator 600 engaging an anvil in preparation for cutting an opening in the target vessel. As shown in FIGS. 8A–8D, external anastomosis operator 700 has a body 710 with an optional handle 720. Attached to body 710 are the main components of operator 700. These main components are cutter 400, spring biasing device 450, an anvil pull engager 500 which includes an anvil pull holder 530 and an anvil pull advancer 560, and an attachment actuator 600.

The attachment actuation devices and the attachment actuator 600 of external operator 700 may be adapted to enable the orientation of the target vessel anastomosis ring 40 and the access tube anastomosis ring 85 relative to each other to remain essentially the same as the rings are brought together to an anastomosis position. Note that once the opposing ring engagers of the attachment actuation devices or the attachment actuator 600 of external operator 700 have engaged the rings of an anastomosis device, preferably in a locked configuration, then the rings are easily brought together while maintaining their relative orientation. The opposing ring engagers may be guided together in a number of different ways. For example, attachment actuation device 600 may rely on guides to bring target vessel anastomosis ring engager 600a and access tube anastomosis ring engager 600b together. Alternatively, a hinge may be used in another embodiment to guide the opposing ring engagers 600a–b together. As discussed below in reference to attachment actuator 600, rail 640 guides the movement of one ring engager to the other. Mechanisms adapted to lock the ring engagers against the rings are also discussed below in reference to attachment actuator 600.

Figure 8B:
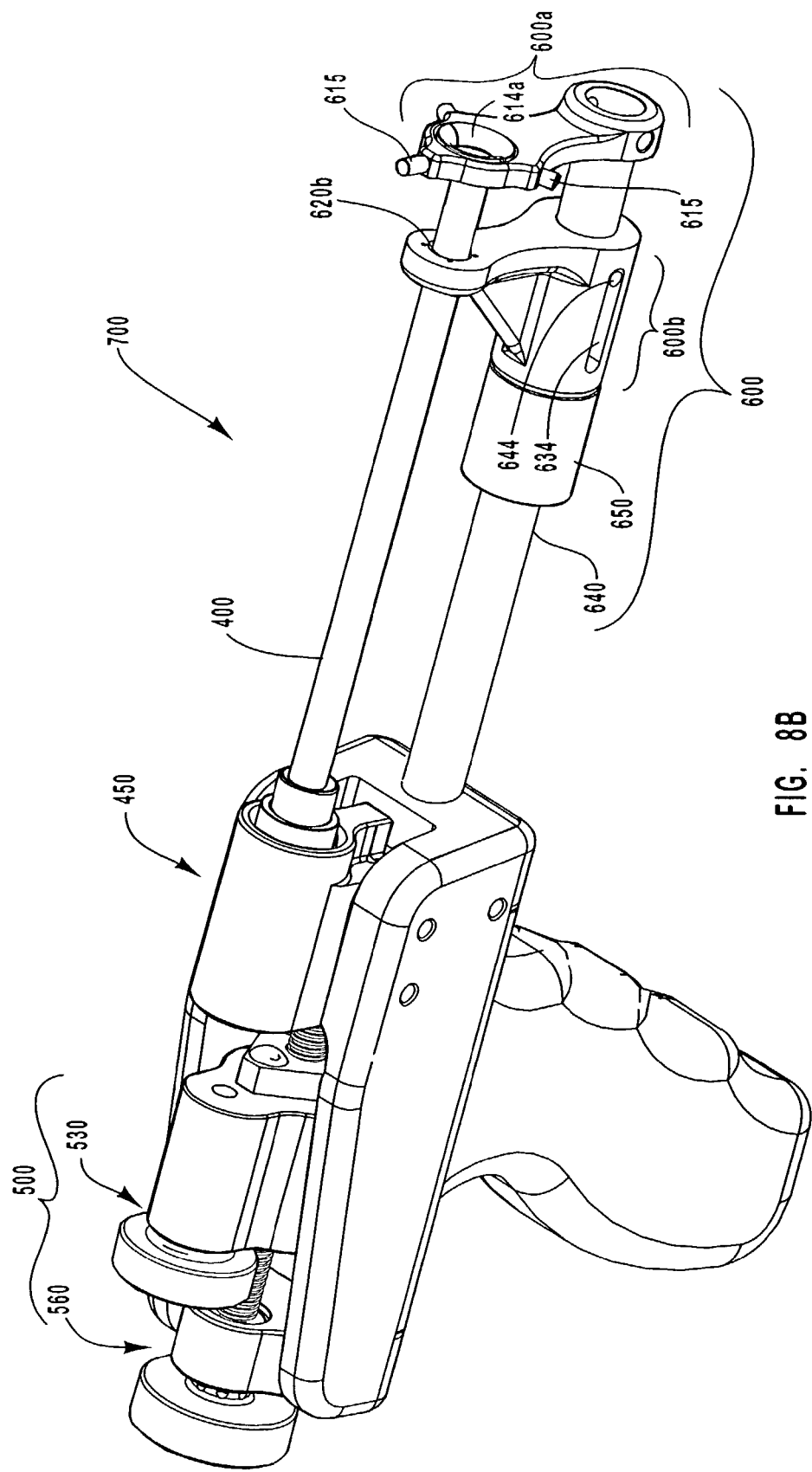
FIG. 8B is a perspective view of the external anastomosis operator.

FIG. 8B provides a perspective view of an external anastomosis operator 700 with its main components identified including: cutter 400, spring biasing device 450, an anvil pull engager 500 which includes an anvil pull holder 530 and an anvil pull advancer 560, and an attachment actuation device 600. Spring biasing device 450 is used to apply pressure against the distal end 418 of cutter 400. One advantage derived from the use of a device such as the external anastomosis operator 700 is that such devices have a series of actuators, and by manipulating these actuators the operator can effectuate the different operations at the anastomosis site without actually having to manually and directly operate each element itself.

Figure 8C:
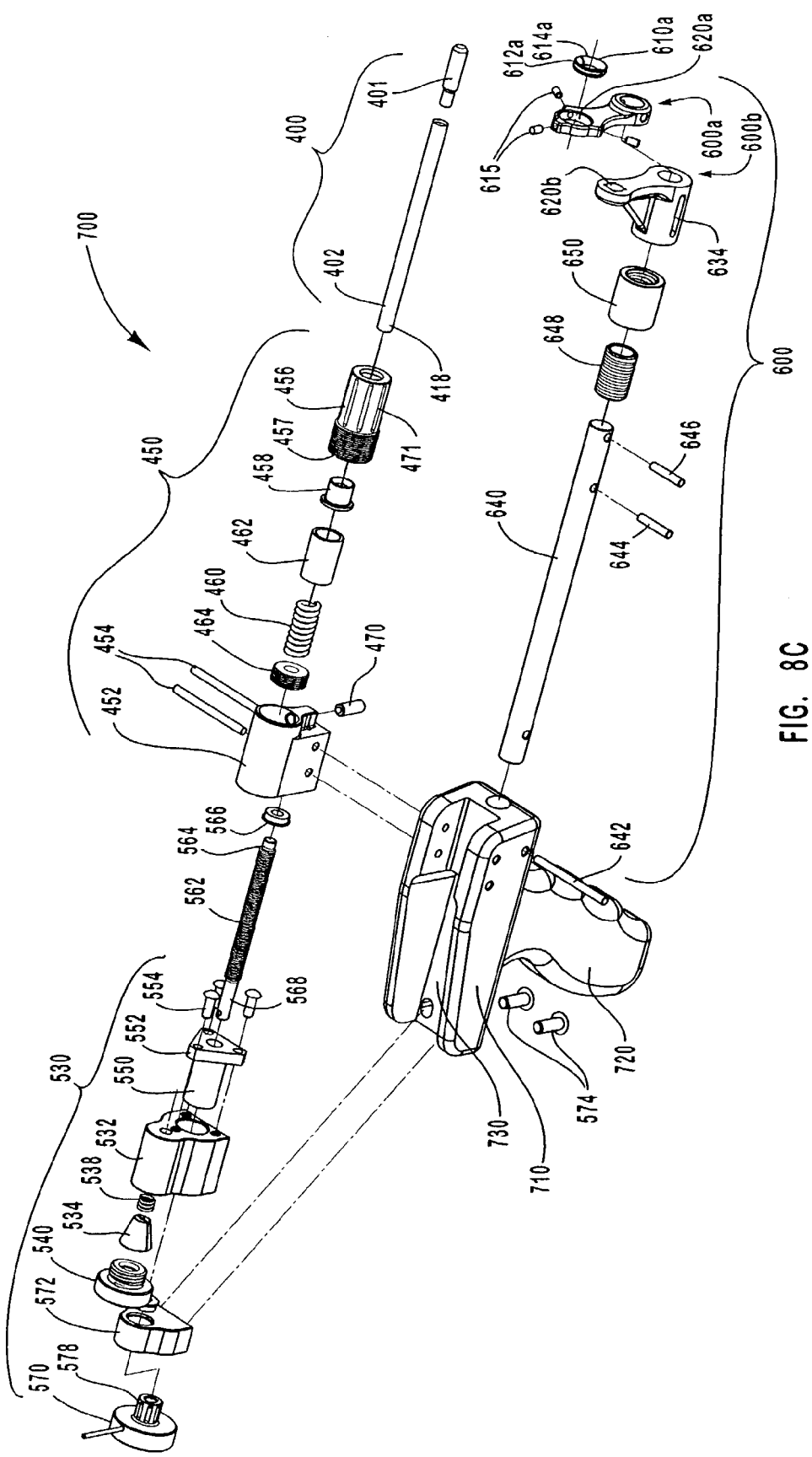
FIG. 8C is an exploded perspective view of the external anastomosis operator.

FIG. 8C provides an exploded perspective view of all of the components of external anastomosis operator 700 so it is with reference primarily to this view that the details of operator 700 are understood. FIGS. 8D–8E provide cross-sectional views of operator 700 depicting the steps for using operator 700.

Cutter 400 is shown in FIG. 8C as including a tip portion 401 and an extension portion 402. A spring biasing device 450 applies pressure against the distal end 418 of cutter 400. Spring biasing device 450 has a spring mount 452 that is mounted to body 710 via spring mount pins 454. A rotatable spring housing 456 is threadably engaged by spring mount 452. Loaded into rotatable spring housing 456 is a cutter cup 458 that is configured to hold distal end 418 of cutter. Cutter cup 458 has a flange that is pushed against a flange at the proximal end of rotatable spring housing 456 such that cutter cup 458 is held in the proximal end of spring housing 456. A spring 460 is positioned within a spring sleeve 462. Spring 460 and spring sleeve 462 have ends that abut cutter cup 458 and opposite ends that abut threaded jam screw 464. Threaded jam screw 464 is accessible via the distal end of spring mount 452 so that it may be rotated to increase or decrease the tension of spring 460 against cutter cup 458.

Cutter cup 458 moves within rotatable spring housing 456 against spring 460. The pressure of spring 460 against cutter cup 458 enables cutter 400 to apply pressure against anvil 210 as anvil 210 is pulled against cutter 400. This makes it easier to cut the vessels as force is being applied in both directions. It also enables cutter 400 to be pushed back by anvil 210 to allow anvil 210 to further distend the wall of vessel 10 as shown in FIGS. 7A–7C until sufficient pressure is applied by spring 460 to bias cutter 400 forward and by the advancement of anvil 210 by anvil pull 230 to cut the vessel. The gradual increase in pressure also serves to assist a spherical engaging end 212 of anvil 210 to self center on cutter 400. More particularly, anvil 210 may be initially misaligned such that the center of engaging end from which anvil pull extends is positioned on the cutting edge of the cutter. A rapid application of pressure would lock such a misalignment while a gradual increase enables the curvature of spherical engaging end to guide the anvil into a centered orientation.

Another function of spring biasing device is to set the position of cutter 400. Rotatable spring housing 456 has a notch 457 at its distal end that enables a screw driver to rotate rotatable spring housing 456 within spring mount 452 to advance or retract rotatable spring housing 456 within spring mount 452. Movement of rotatable spring housing 456 also moves cutter cup 458, thereby determining the location of distal end 418 of cutter 400 within operator 700. Of course advancement of cutter cup 458 towards the proximal end of operator 700 causes cutting knife 400 to engage anvil 210 closer to target vessel anastomosis ring 40 while retraction of cutter cup 458 towards the distal end of operator 700 causes cutting knife and anvil to engage each other closer to access tube anastomosis ring 85. The position of cutter 400 is preferably set to enable vessel 10 to be distended in a manner that is optimal for then subsequently everting the portion defining the newly formed opening onto holding tabs 46. To carefully identify the length that rotatable spring housing 456 is advanced or retracted, a detent 470 is threaded into spring mount such that it can contact rotatable spring housing and engage the grooves 471 of rotatable spring housing in a manner that enables detent 470 to click as each groove is rotated past detent 470.

Obviously spring biasing device 450 has many variables that impact the manner in which cutter 400 is used in combination with external anastomosis operator 700. Some of these variables include the inherent tension of spring 460, the tension of spring 460 as caused by the position of threaded jam screw 464 in spring mount 452 against spring 460, and the position of the surface which distal end 418 of cutter 400 abuts, namely cutter cup 660 as determined by the position of rotatable spring housing 456 within spring mount 452.

Spring biasing device 450 is an example of spring biasing means for providing tension against the cutting means as the cutting means engages the anvil means of the intraluminally directed anvil apparatus. The spring biasing means provides an amount of tension that enables the cutting means to form the vessel opening after the wall of the target vessel has been distended by the action of the anvil means being pulled into the openings of the ring assembly such that forming the target vessel opening results in at least partial eversion of the portion of the first vessel defining the first vessel opening.

As indicated above, anvil pull engager 500 has two primary components including an anvil pull holder 530 and anvil pull advancer 560. Anvil pull holder 530 receives anvil pull 230 via spring biasing device 450. More particularly, anvil pull 230 extends through cutter cup 458, rotatable spring housing 456, spring 460 and sleeve 462 around spring 460, and out of threaded jam screw 464.

Anvil pull holder 530 includes a holder mount 532 positioned in track 730 of body 710. In this embodiment, the holder mount is moveable so that the anvil pull can be advanced after it is held. However, in other embodiments, the anvil pull holder may just lock the anvil pull into position such that the cutter is moved against a stationary anvil. Similarly, the spring biasing device 450 may be eliminated so that the vessel is cut only by pressure exerted by the anvil pull against the cutter. As discussed above, while the cutter and the anvil may engage each other in these arrangements, it is preferable for the cutter to apply some pressure as the anvil pull is advanced against the cutter.

Holder mount 532 may be utilized in different ways to hold anvil pull 230. Holder 530 has a split cone 534 inserted into a tapered chamber (not shown) against a spring 538. Anvil pull 230 extends through apertures in holder mount 532, spring 538, split cone 534 and out of an aperture centered in holder knob 540. Holder knob 540 is threadably engaged by holder mount 532 such that rotation of holder knob 540 advances split cone 534 in the tapered chamber, causing split cone to lock onto anvil pull 230. Holder mount may be slotted at its distal end, as may holder knob. By aligning the slot (not shown) in holder knob 540 with an insert slot (not shown) in holder mount 532, anvil pull 230 can be bent so that it extends through both the holder knob slot and the insert slot. Holder knob 540 can then be rotated so that the bent portion of anvil pull 230 is rotated into one of the locking slots that extend perpendicularly from the insert slot. This securely locks anvil pull 230 into position. Anvil pull 230 can be locked through the use of slots instead of or in addition to the use of split cone 534 in the tapered chamber.

Since anvil pull holder 530 is moveable, it threadably engages rotatable lead screw 562 of anvil pull advancer. More particularly, lead screw 562 is threadably engaged by anti-backlash nut 550 which is fixedly attached to holder mount 532. Anti-backlash nut 550 has an attachment face 552 through which a plurality of attachment face screws 554 extend to hold holder mount 532 and anti-backlash nut 550 together.

Lead screw 562 has a proximal pivot end 564 that rotates within a bushing 566 positioned within a recess in spring mount 452. Lead screw also has a distal pivot end 568 that is attached to advancer knob 570 to rotate lead screw 562. Advancer knob 570 rotates within an advancer knob mount 572 which is attached to body 710 in groove 730 via advancer knob mount bolts 574. As shown in FIG. 8D, distal pivot end 568 rotates in a bushing 576 positioned within an aperture of advancer knob mount 572.

Advancer knob 570 has a stem with a plurality of grooves 578 that engage a detent (not shown) to click so that the incremental rotation of advancer knob 570 can be carefully counted to determine the length that the anvil is moved in the anastomosis device as the anvil pull is advanced. The detent is threaded into advancer knob mount 572 such that it can contact grooves 578 in the stem of advancer knob 570 to click as each groove is rotated past the detent.

FIG. 8D–8E depict advancer knob 570 being rotated to move anvil pull advancer 560 so that it can urge anvil pull 230 in a manner such that anvil 210 is advanced within target vessel anastomosis ring 40. As advancer knob 570 is rotated, lead screw 562 is thereby rotated. Since anvil pull holder 530 is threadably engaged on rotatable lead screw 562 and is locked in track 730, anvil pull holder 530 can only move forward and backward as lead screw 562 is rotated.

FIG. 8E depicts attachment actuation device 600 prior to being engaged. Attachment actuation device 600 has a target vessel anastomosis ring engager 600a and a second access tube anastomosis ring engager 600b. Target vessel anastomosis ring engager 600a may utilize an optional adaptor 610a to engage the target vessel anastomosis ring 40, as shown in FIG. 8C. Removing adaptor 610a after anastomosis by loosening set screws 615 enables operator 700 to be pulled off of access tube apparatus 100. Target vessel anastomosis ring engager 600a and access tube anastomosis ring engager 600b each have a cutter aperture 620a and 620b. Cutter 400 extends through these aligned apertures 620a–b. Target vessel anastomosis ring engager 600a is positioned on rail 640 such that it extends slightly beyond cutting edge 414 of cutter 400, as shown in FIG. 8D. This difference in length enables target vessel anastomosis ring 40 to be held slightly beyond cutter in a manner that permits the wall of the target vessel to be pulled into anastomosis device as shown in FIGS. 7A–7D and distended as needed.

Rail 640 is attached to body 710 via rail pin 642. A groove pin 644 extends through rail 640. An anastomosis ring holder 646 holds the target vessel anastomosis ring engager 600a on the proximal end of rail 640.

Target vessel anastomosis ring engager 600a is fixedly mounted on rail 640 via pin 646 while access tube anastomosis ring engager 600b is movably mounted on rail 640. Access tube anastomosis ring engager 600b has a groove 634 through which groove pin 644 extends. The configuration of groove pin 644 in groove 634 enables access tube anastomosis ring engager 600b to be held in a fixed orientation such that it can be moved back and forth as needed with respect to target vessel anastomosis ring, engager 600a.

Access tube anastomosis ring engager is moved on rail 640 by rotating threaded compressor sleeve 650 which engages a threaded rail sleeve 648. Threaded rail sleeve 648 may be adhered onto rail 640 or be an integral component. Rail 640 and its threaded rail sleeve 648 or threaded rail portion combined with compressor sleeve 650 are means for advancing one ring engager towards the other ring engager.

Set screws 615 may be used without adaptor 610a to lock target vessel anastomosis ring engager 600a on target vessel anastomosis ring 40. Access tube anastomosis ring engager 600b may have an optional latch (not shown) that enables engager 600b to lock onto access tube anastomosis ring 85. Such a latch is not required since access tube anastomosis ring engager 600b is sized to push against access tube anastomosis ring 85. Once the anastomosis is complete, set screws 615 and the latch are released to release the anastomosis and access tube anastomosis ring engagers from the rings. Note that there are many other ways for locking the rings with anastomosis and access tube anastomosis ring engagers 600a–b such as the use of conventional quick release configurations. Quick release configurations, latches and set screws are all examples of means for locking the ring engagers against the rings.

The anastomosis device is preferably used for vascular anastomosis, however, the present invention is not limited to such use. Nor is the anastomosis device limited to use with any particularly sized vessel or access tube. For example, vessels and access tubes may be anastomosed with diameters ranging from about 2 mm to about 20 mm, but there is no fundamental limitation for using embodiments of this invention with vessels or access tubes with diameters less than 2 mm.

It will be obvious to those having skill in the art that many changes may be made to the details of the above-described embodiments of this invention without departing from the underlying principles thereof. The scope of the present invention should, therefore, be determined only by the following claims.

The invention claimed is:

1. A method for percutaneously and repeatedly accessing a body fluid such as blood in an anatomical vessel, comprising:
   obtaining an access tube having an access end and an anastomosis end with a conduit extending from the access end to the anastomosis end;
   anastomosing the anastomosis end of the access tube to the sidewall of an anatomical vessel, wherein the access tube has sufficient length so that the access tube extends percutaneously with the access end being extracorporeally positioned;
   occluding the conduit of the access tube with an occluder at the anastomosis end;
   removing the occluder to provide fluid communication between the lumen of the anatomical vessel and the conduit of the access tube;
   re-occluding the conduit of the access tube; and
   flushing the conduit with a flushing fluid after the conduit of the access tube has been re-occluded.

2. The method of claim 1, wherein the occluder has an exposed portion that is exposed to the lumen and in contact with body fluid in the lumen once the occluder is positioned in the conduit; and wherein the anastomosing and occluding steps are achieved with configurations that result in minimal contact between the body fluid and materials other than the native vessel walls once the conduit is occluded as only the exposed portion of the occluder is in significant contact with the fluid during occlusion.

3. The method of claim 2, wherein the occluder abuts the vessel wall when the occluder is in its occluding position such that the exposed portion of the occluder extends all the way to the end of the access tube conduit and is approximately flush with the vessel wall.

4. The method of claim 1, wherein the occluder has an exposed portion that is exposed to the lumen and in contact with body fluid in the lumen once the occluder is positioned in the conduit; and wherein the surface area of the exposed portion is primarily determined by the circumference of the conduit.

5. The method of claim 1, wherein the anastomosing is done by suturing.

6. The method of claim 1, wherein reoccluding the conduit comprises replacing the occluder with another occluder.

7. The method of claim 1, further comprising providing fluid communication between the conduit of the access tube and a blood treatment device.

8. The method of claim 7, further comprising providing fluid communication between the blood treatment device and a second access tube anastomosed to a second vessel to re-introduce the treated blood.

9. The method of claim 7, further comprising providing fluid communication between the blood treatment device and a second access tube anastomosed to the vessel at another location to re-introduce the treated blood.

10. The method of claim 7, further comprising re-introducing the treated blood back through the conduit of the access tube.

11. The method of claim 1, further comprising replacing a portion of the occluder with a new portion, wherein at least a portion of the replaced portion is exposed to flow in the vessel.

12. The method of claim 1, further comprising flushing out the portion of the access tube conduit between the occluder and the interior conduit wall with a flushing fluid while the occluder is positioned in the conduit.

13. The method of claim 12, wherein the flushing fluid is an antibacterial solution.

14. The method of claim 1, wherein the occluder has an exposed portion that is exposed to the lumen and in contact with body fluid in the lumen once the occluder is positioned in the conduit; and wherein the exposed portion of the occluder is coated with a pharmacological substance.

15. The method of claim 14, wherein the pharmacological substance elutes a pharmacological agent at the exposed portion of the occluder.

16. The method of claim 14, wherein the pharmacological substance comprises at least one of an anticoagulant agent, an antimicrobial agent, an antiproliferative agents.

17. A method for percutaneously and repeatedly accessing a body fluid such as blood in an anatomical vessel, comprising:
   obtaining an access tube having an access end and an anastomosis end with a conduit extending from the access end to the anastomosis end;
   anastomosing the anastomosis end of the access tube to the sidewall of an anatomical vessel, wherein the access tube has sufficient length so that the access tube extends percutaneously with the access end being extracorporeally positioned;
   occluding the conduit of the access tube at the anastomosis end with an occluder after the anastomosis end of the access tube has been anastomosed to the sidewall of the anatomical vessel;
   removing the occluder to provide fluid communication between the lumen of the anatomical vessel and the conduit of the access tube;
   providing fluid communication between the access end of the access tube and a device to enable a fluid to flow from the conduit of the access tube to the device;
   re-occluding the conduit of the access tube; and
   flushing the conduit with a flushing fluid after the conduit of the access tube has been re-occluded.

18. The apparatus of claim 17, wherein the occluder has an occlusion end having an exposed portion that is exposed to the lumen of the vessel and in contact with body fluid in the lumen once the occluder is positioned in the conduit, and wherein the surface area of the exposed portion is primarily determined by the circumference of the conduit.

19. An apparatus for facilitating repeated percutaneous access to a body fluid such as blood in an anatomical vessel, comprising:
   an access tube having an access end and an anastomosis end with a conduit extending from the access end to the anastomosis end, wherein the anastomosis end is configured to be attached to the sidewall of a vessel at an anastomosis opening, and wherein the access end is configured to extend percutaneously and be extracorporeally accessible; and
   an occluder configured to fit within the access tube conduit to control fluid flow between the anatomical vessel and the access tube, wherein the occluder is removable from the conduit while the access tube remains attached to the vessel;
   wherein the apparatus is configured to enable a flushing fluid to be delivered into the access tube after the access tube has been re-occluded by the occluder.

20. The apparatus of claim 19, wherein the occluder has an exposed portion at its occlusion end that is in contact with body fluid in the lumen once the occluder is positioned in the conduit.

21. The apparatus of claim 20, wherein the occluder is configured such that there is minimal contact between the body fluid and materials other than the native vessel walls once the conduit is occluded as only the exposed portion of the occluder is in significant contact with the body fluid during occlusion.

22. The apparatus of claim 19, wherein the access tube further comprises a component of an anastomosis device at the anastomosis end of the access tube.

23. The apparatus of claim 22, wherein the component is an anastomosis ring.

24. The apparatus of claim 19, wherein the occluder has a stemmed portion such that the occluder has a larger diameter at its occlusion end than at the stemmed portion of the occluder.

25. The apparatus of claim 19, wherein occluder is uniformly-shaped.

26. The apparatus of claim 19, wherein the conduit has a tapered diameter that is slightly smaller at the anastomosis end than at the access end such that a tighter seal is maintained between the conduit and the occluder at the anastomosis end than at the access end.

27. The apparatus of claim 19, wherein the occluder has a sealing lip extending circumferentially around at least a portion of the occluder, and wherein the sealing lip has a diameter greater than the diameter of other portions of the occluder fitting inside the conduit.

28. The apparatus of claim 27, wherein the conduit is flexible such that its diameter can be stretched beyond a resting diameter, wherein the resting diameter of the conduit is the diameter at times during which the conduit is not subjected to stretching forces.

29. The apparatus of claim 28, wherein the sealing lip has a diameter larger than the resting diameter of the conduit such that the sealing lip forms a bulge around the conduit when the occluder is inside the conduit.

30. The apparatus of claim 19, wherein the access end of the access tube is connectable to a control end of the occluder.

31. The apparatus of claim 19, wherein the occluder has a channel contained therein, wherein the channel has a first opening and a second opening, and wherein the channel is configured to enable the flushing fluid to be introduced through the first opening and to flow out of the second opening to flush out the portion of the conduit between the occluder and an interior conduit wall.

32. The apparatus of claim 19, wherein the occluder is configured to avoid extending significantly into the vessel lumen.

33. The apparatus of claim 20, wherein the occluder is configured to abut the vessel wall when the occluder is in its occluding position such that the exposed portion of the occlusion end is approximately flush with the surrounding vessel wall.

34. The apparatus of claim 19, further comprising a pharmacological coating on the occluder.

35. The apparatus of claim 34, wherein the pharmacological coating includes an antiproliferative agent.

36. The apparatus of claim 19, further comprising a pharmacological coating on one or more surfaces inside the conduit of the access tube.

37. An apparatus for facilitating repeated percutaneous access to a body fluid such as blood in an anatomical vessel, comprising:
   access tube means for accessing an anastomosed vessel, wherein the access tube means has an access end and an anastomosis end with a conduit extending from the access end to the anastomosis end, wherein the anastomosis end is configured to be attached to the sidewall of a vessel, and wherein the access end is configured to extend percutaneously and be extracorporeally accessible; and
   occluding means for blocking fluid communication between the vessel and the access tube, wherein the occluding means can be selectively removed from the access tube means to allow for fluid communication between the vessel and the access tube means;
   wherein the apparatus is configured to enable a flushing fluid to be delivered into the access tube means after the access tube means has been re-occluded by the occluding means.

38. The apparatus of claim 37, wherein the occluding means is configured to allow for minimal contact between the body fluid and materials other than the native vessel walls once the conduit is occluded as only an exposed portion of the occluding means is in significant contact with the body fluid during occlusion.

39. The apparatus of claim 38, wherein the exposed portion of the occluding means is replaceable.

40. The apparatus of claim 37, further comprising at least one means for facilitating anastomosis of the access tube means to an anatomical vessel.

41. The apparatus of claim 40, wherein the at least one means for facilitating anastomosis of the access tube means to an anatomical vessel is an anastomosis ring.

42. The apparatus of claim 37, wherein the occluding means has a sealing portion having a diameter greater than the diameter of other portions of the occluding means.

43. The apparatus of claim 37, wherein the access end of the access tube means is connectable to the occluding means.

44. The apparatus of claim 37, wherein the occluding means has a channel contained therein, wherein the channel has a first opening and a second opening and wherein the channel is configured to enable the flushing fluid to be introduced through the first opening and to flow out of the second opening to flush out the portion of the conduit between the occluding means and an interior conduit wall.

45. The apparatus of claim 37, further comprising means for preventing infection in the access tube means.

46. The apparatus of claim 37, further comprising means for preventing complications at the anastomosis site.

47. The apparatus of claim 46, wherein the means for preventing complications comprises a pharmacological coating on the occluding means.

* * * * *